United States Patent
Boyanov et al.

(10) Patent No.: US 10,961,576 B2
(45) Date of Patent: *Mar. 30, 2021

(54) HYBRID NANOPORE SENSORS

(71) Applicant: Illumina, Inc., San Diego, CA (US)

(72) Inventors: Boyan Boyanov, San Diego, CA (US); Jeffrey G Mandell, San Diego, CA (US); Kevin L Gunderson, San Diego, CA (US); Jingwei Bai, San Diego, CA (US); Liangliang Qiang, San Diego, CA (US); Bradley Baas, Madison, WI (US)

(73) Assignee: Illumina, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/707,554

(22) Filed: Dec. 9, 2019

(65) Prior Publication Data
US 2020/0190577 A1 Jun. 18, 2020

Related U.S. Application Data

(63) Continuation of application No. 15/522,987, filed as application No. PCT/US2015/042680 on Jul. 29, 2015, now Pat. No. 10,519,499.

(60) Provisional application No. 62/157,749, filed on May 6, 2015, provisional application No. 62/031,762, filed on Jul. 31, 2014.

(51) Int. Cl.
*C12Q 1/6874* (2018.01)
*G01N 33/487* (2006.01)
*G01N 27/447* (2006.01)

(52) U.S. Cl.
CPC ..... *C12Q 1/6874* (2013.01); *G01N 27/44782* (2013.01); *G01N 27/44791* (2013.01); *G01N 33/48721* (2013.01)

(58) Field of Classification Search
None
See application file for complete search history.

(56) References Cited

U.S. PATENT DOCUMENTS

| | | | |
|---|---|---|---|
| 6,015,714 A | 1/2000 | Baldarelli | |
| 8,277,628 B2 | 10/2012 | Ronaghi | |
| 8,652,779 B2 | 2/2014 | Turner | |
| 8,673,550 B2 | 3/2014 | Gundlach | |
| 8,999,716 B2 | 4/2015 | Gundlach | |
| 2006/0231419 A1 | 10/2006 | Barth | |
| 2008/0254995 A1 | 10/2008 | Kim | |
| 2010/0084276 A1 | 4/2010 | Lindsay | |
| 2010/0196203 A1 | 8/2010 | Sanghera | |
| 2010/0331194 A1* | 12/2010 | Turner et al. | G01N 27/447 506/2 |
| 2013/0146480 A1* | 6/2013 | Garaj et al. | G01N 27/447 205/787 |
| 2014/0051069 A1 | 2/2014 | Jayasinghe | |
| 2014/0200158 A1 | 7/2014 | Bowen | |
| 2015/0005447 A1 | 1/2015 | Berti | |

FOREIGN PATENT DOCUMENTS

| | | |
|---|---|---|
| CN | 103154729 | 6/2013 |
| WO | WO 2006/100484 | 9/2006 |
| WO | WO 2013/016486 | 1/2013 |
| WO | WO 2013/057495 | 4/2013 |

OTHER PUBLICATIONS

De la Torre et al., Fabrication and Characterization of Solid-state Nanopore Arrays for High Throughput DNA Sequencing, *Nanotechnology*, 23(38):385308 (2012).
Deamer et al., Characterization of Nucleic Acids by Nanopore Analysis, *Acc Chem Res*., 35:817-825 (2002).
Deamer et al., Nanopores and nucleic acids: prospects for ultrarapid sequencing, *Trends Biotechnol.*, 18:147-151 (2000).
Denisov et al., Directed Self-Assembly of Monodisperse Phospholipid Bipayer Nanodiscs with Controlled Size, *J. Am. Chem. Soc.* 126, 3477-3487 (2004).
Derrington et al., Nanopore DNA sequencing with MspA, *Proc. Natl. Acad. Sci. USA*, 107:16060 (2010).
Folkers et al., Self-Assembled Monolayers of Long-Chain Hydroxamic Acids on the Native Oxides of Metals, *Langmuir* 11:813 (1995).
Garalde et al., Distinct Complexes of DNA Polymerase I (Klenow Fragment) for Base and sugar Discrimination during Nucleotide Substrate Selection, *J. Biol. Chem.* 286: 14480-14492 (2011).
Giess et al., The Protein-Tethered Lipid Bilayer: A Novel Mimic of the Biological Membrane, *Biophysical J.* 87:3213-3220 (2004).
Howorka et al, Kinetics of Duplex formation for individual DNA strands within a single protein nanopore, *PNAS* 98: 12996-13301 (2001).
Howorka et al, Sequence-specific detection of individual DNA strands using engineered nanopores, *Nature Biotechnology* 19: 636-639 (2001).
Howorka et al, Probing Distance and Electrical Potential within a Protein Pore with Tethered DNA, *Biophysical Journal* 83: 3202-3210 (2002).
Hurt et al., Specific Nucleotide Binding and Rebinding to Individual DNA Polymerase Complexes Captured on a Nanopore, *JACS* 131: 3772-3778 (2009).
Kim et al., Detecting single-abasic residues within a DNA strand immobilized in a biological nanopore using an integrated CMOS sensor, *Sens. Actuators B Chem.* 177: 1075-1082 (2012).
Kwok et al., Nanopore Fabrication by Controlled Dielectric Breakdown, *PLOS One* 9(3):e92880 (2014).

(Continued)

*Primary Examiner* — Kaijiang Zhang
(74) *Attorney, Agent, or Firm* — Knobbe, Martens, Olson & Bear LLP

(57) ABSTRACT

The disclosure provides detection apparatus having one or more nanopores, methods for making apparatus having one or more nanopore and methods for using apparatus having one or more nanopores. Uses include, but are not limited to detection and sequencing of nucleic acids.

20 Claims, 11 Drawing Sheets

(56) References Cited

OTHER PUBLICATIONS

Li et al., DNA molecules and configurations in a solid-state nanopore microscope *Nat Mater.*, 2(9):611-615 (2003).
Montal and Mueller, Formation of Bimolecular Membranes from Lipid Monolayers and a Study of Their Electrical Properties, *Proc. Natl. Acad. Sci. USA.*, 1972; 69: 3561-3566.
Nath et al., Applications of Phospholipid Bilayer Nanodiscs in the Study of Membranes and Membrane Proteins, *Biochemistry* 46, 2059-2069 (2007).
Olsen et al, Electronic Measurements of Single-Molecule Processing by DNA Polymerase I (Klenow Fragment), *JACS* 135: 7855-7860 (2013).
Patterson et al., Controlled fabrication of nanopores using a direct focused ion beam approach with back face particle detection, *Nanotechnology* 19, 235304 (2008).
Peters, The Nanopore Connection to Cell Membrane Unitary Permeability, *Traffic* 6(3):199-204 (2005).
Powell et al., Electric-field-induced wetting and dewetting in single hydrophobic nanopores, *Nature Nanotechnology* 6, 798-802 (2011).
Rakhmatullina et al., Solid-Supported Block Copolymer Membranes through Interfacial Adsorption of Charged Block Copolymer Vesicles, *Langmuir* 24:6254-6261 (2008).
Raschle et al., Structural and functional characterization of the integral membrane protein VDAC-1 in lipid bilayer nanodiscs, *J. 15 Am. Chem. Soc.* 131: 17777-17779 (2009).
Rosenstein et al., Integrated nanopore sensing platform with sub-microsecond temporal resolution, *Nature Methods* 9:487-492 (2012).
Rosenstein et al., Single Ion Channel Recordings with CMOS-Anchored Lipid Membranes, *Nano Lett* 13,2682-2686 (2013).
Soni et al., Synchronous optical and electrical detection of biomolecules traversing through solid-state nanopores, *Rev Sci Instrum.*, 81(1):014301 (2010).
Stackmann, Supported Membranes: Scientific and Practical Applications, *Science* 271:43-48 (1996).
Steinem et al. Impedance analysis of supported lipid bilayer membranes: a scrutiny of different preparation techniques, *Biochim. Biophys. Acta*, 1279: 169-180 (1996).
Storm et al., Fabrication of solid-state nanopores with single-nanometre precision, *Nature Materials* 2:537-540 (2003).
Uddin et al., Integration of solid-state nanopores in a 0.5um cmos foundry process, *Nanotechnology* 24(15): 155501 10 (2013).
Vallejo, Impedance analysis of ion transport through gramicidin channels in supported lipid bilayers, *Bioelectrochemistry* 57: 1-7 (2002).
Waggoner et al., Increasing the speed of solid-state nanopores, *Journal of Vacuum Science & Technology B* 29, 032206 (2011).
Wang et al., Single-molecule DNA detection using a novel SP1 protein nanopore, *Chem. Commun.*, 49:1741-5 1743 (2013).
White et al., Single Ion-Channel Recordings Using Glass Nanopore Membranes, *J Am Chem Soc* 129: 11766-11775 (2007).
Yang et al., Rapid and precise scanning helium ion microscope milling of solid-state nanopores for biomolecule detection, *Nanotechnology* 22, 285310 (2011).
Yusko et al., Controlling the translocation of proteins through nanopores with bioinspired fluid walls, *Nat Nanotechnol* 6(4): 253-260 (2011).
Baas, "Characterization of monomeric human cytochrome P450 3A4 and cytochrome P450 reductase in nanoscale phospholipid bilayer discs", "2.2.4 Self-Assembly of Empty and CYP3A4-Containing Nanodiscs", University of Illinois at Urbana-Champaign, US.A, Jul. 18, 2006.
Hall, et al, Hybrid pore formation by directed insertion of alpha hemolysin into solid-state nanopores, Nat Nanotechnol 5(12):874-877 (2010).

\* cited by examiner

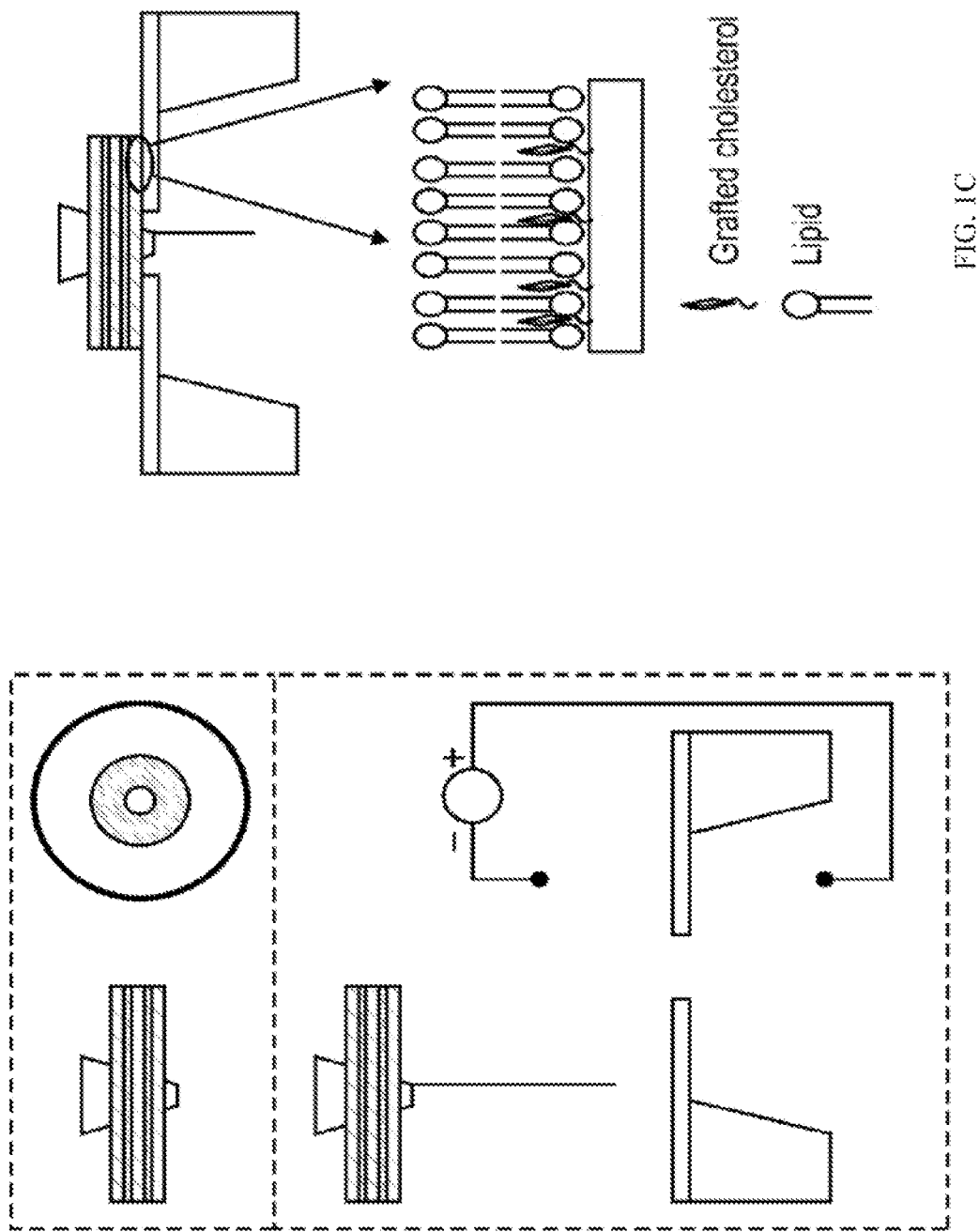

SELF-ASSEMBLY OF NANODISCS

HYBRID NANOPORE SENSORS

CROSS-REFERENCE TO RELATED APPLICATIONS

This application is a continuation of U.S. application Ser. No. 15/522,987 filed Apr. 28, 2017 which is the U.S. national phase of PCT/US2015/042680 filed Jul. 29, 2015 and published in English as WO 2016019030 on Feb. 4, 2016 which claims the benefit of U.S. Provisional Application No. 62/157,749, entitled "TETHERED NANOPORES, NANOPORES IN NANODISCS AND HYBRID NANOPORE SENSORS" and filed May 6, 2015, and U.S. Provisional Application No. 62/031,762, entitled "NANOPORES IN NANODISCS AND HYBRID NANOPORE SENSORS," filed Jul. 31, 2014, the disclosures of which are incorporated herein by reference in their entireties for all purposes.

STATEMENT REGARDING FEDERALLY SPONSORED R&D

This invention was made with Government support under National Institute of Health (NIH) Grant Number 5R21HG007833-02 awarded by the Public Health Services (PHS). The Government has certain rights in the invention.

BACKGROUND

Protein nanopore devices have been explored for many sensor applications, especially in the field of DNA/RNA sequencing. Discrimination of nucleotide bases has been demonstrated by reading the ionic current signal when the DNA molecule is passing through the nanopore. Following from these initial observations, protein based nanopore devices have been postulated to have great potential to push forward nucleic acid sequencing technology in terms of lower price, fast turn around and longer read length.

A more mature technology, sequencing-by synthesis (SBS), has made rapid progress in the last five years, doubling throughput about every six months, far outpacing Moore's law for the semiconductor industry. This rapid progress has been enabled by primarily three key improvements to SBS protocols: (1) cycle sequencing chemistry improvements; (2) increases in density of nucleic acid colonies on surfaces; and (3) improvement in imaging/scanning technology. These three technological improvements have increased throughput of commercial systems from about 1 Gb per run in January 2007 to over 1 Tb per run in June 2012. However, these technological advances have not been found to be directly portable to nanopore technologies.

In spite of this rapid progress in SBS improvement, 30× genome prices are still over $1000/genome with turn-around times in excess of a week. Moreover, de novo assembly and haplotyping of human genomes obtained via SBS is challenged by short reads. Strand sequencing via nanopores, can potentially read up to 50,000 bases within a few minutes. This single molecule platform to date appears to achieve speed but at the cost of greatly decreased parallelization.

Parallelization of biological nanopores is notoriously difficult. The fragility of the platform itself, especially the semi-fluidic nature of the lipid bilayer, demands specialized handling often by highly trained technicians, making nanopore systems less practical for wide spread commercialization. The current technique for assembly of protein nanopore devices is mostly manual, laborious and time consuming. After painting a lipid bilayer over a substrate having an array of micrometer sized apertures, the operator contacts the coated array with a solution having a carefully titrated quantity of the protein. The amount of nanopore is selected according to Poisson statistics to maximize the number of apertures that acquire a nanopore while minimizing the number of apertures that are loaded with greater than one nanopore. After a specific incubation period has lapsed, the nanopore-containing solution is washed away. Poisson loading requires the time period to be carefully selected to achieve the highest possible number of apertures having one and only one nanopore. The results are highly dependent upon the skill of the operator and not easily adaptable to large scale device manufacturing.

Thus, a major challenge for nanopore technology is to increase the robustness of the platform and simultaneously improve parallelization, for example, in sequencing applications. The present disclosure addresses this need and provides other advantages as well.

BRIEF SUMMARY

The details of one or more embodiments are set forth in the accompanying drawings and the description below. Other features, objects, and advantages will be apparent from the description and drawings, and from the claims.

The present disclosure provides a hybrid nanopore consisting of a protein nanopore inserted in a solid state nanopore. In particular embodiments, the hybrid nanopore is created with and ultimately includes protein nanopores inserted in lipid nanodiscs. In accordance with the methods set forth herein the nanopore-containing lipid nanodiscs can be self-assembled.

In particular embodiments, a protein nanopore is initially self-assembled within a lipid nanodisc in free solution, as shown in FIG. 1A; then the protein nanopore is grafted with a nucleic acid as shown in FIG. 1B; then electrophoretic force is used to drive the nucleic acid chain through the solid-state nanopore until the protein nanopore-containing nanodisc comes in contact with the solid state nanopore surface as shown in FIG. 1C.

Non-limiting advantages of the lipid nanodisc assisted nanopore assembly scheme of the present disclosure, when compared to typical nanopore fabrication technologies that are based on suspended lipid membrane include, for example:

(1) Structural stability: the protein nanopore is inserted in a hybrid membrane and the solid nanopore supports most of the membrane and provides a nanometer-sized aperture.

(2) Scalable fabrication: the nature of the interactions between the protein nanopore-containing lipid nanodisc and the solid state nanopore are self-limiting such that fabrication is far less fickle than assembly methods that rely on Poisson loading of nanopores into solid-state apertures. Insertion of a single protein nanopore into the bilayer can be accomplished during reconstitution into a lipid nanodisc. The lipid nanodisc's size (e.g. 10-13 nm in some embodiments) can be selected to favor incorporation of only a single protein nanopore (e.g. ~5 nm Msp pore). Furthermore, the solid state nanopore size (e.g. 7-10 nm diameter aperture in some embodiments) can be selected to allow for assembly of only one protein-nanodisc complex per solid-state nanopore aperture. Thus in many embodiments, there is no need for active monitoring of electrical characteristics during assembly and screening of multiple insertions.

(3) Better electrical insulation: direct insertion of a protein nanopore in a solid-state nanopore typically requires detailed matching of the size and shape between the two nanopores to achieve adequate ionic current isolation. In the presently disclosed methods, the lipid nanodisc can merely be selected to be larger than the entrance of the solid state nanopore. Current leakage can be prevented by a wide range of nanodisc sizes above a minimum value such that avoiding current leakage will no longer require detailed shape matching between protein and solid state nanopores.

(4) Relaxed fabrication requirements for solid state nanopores: solid-state nanopores having pore diameter greater than 5 nm can form functional hybrid nanopores with protein nanopore-containing lipid nanodiscs. This feature size is readily achievable by state-of-art semiconductor technology, whereas leading-edge pore fabrication, required for creating solid state nanopores having diameters in the 2-3 nm range required for direct insertion of protein nanopores, is highly variable, costly and overly dependent on operator skill.

(5) Allows massive parallelization: elimination of micron-sized lipid membranes can allow a solid-state nanopore platform to achieve a high degree of parallelization via integration with on-chip amplifiers and data acquisition circuits. Exemplary amplifiers, circuits and other hardware useful for data acquisition are described in U.S. Pat. No. 8,673,550 or 8,999,716; Rosenstein et al., Nano Lett 13, 2682-2686 (2013); or Uddin et al., Nanotechnology 24, 155501 (2013), each of which is incorporated herein by reference.

(6) Lower intrinsic noise: solid-state nanopores typically require proper wetting for stable transconductance. Since the solid-state nanopore is only utilized as a mechanical support in particular embodiments of the system set forth herein those embodiments will be expected to exhibit lower noise than a standalone solid-state nanopore.

The present disclosure describes methods for making hybrid nanopores combining top-down patterning and nanofabrication of solid-state nanopores with bottom-up biological assembly of protein nanopores. Existing techniques for nucleic acid sequencing with nanopore, especially biological nanopores in lipid bilayers, achieve high speed and read length at the cost of greatly decreased parallelization and data throughput. The fragility of the existing platforms also make them less practical in commercialization. The compositions and methods of the present disclosure can overcome these limitations by establishing a hybrid biological-solid state structure that can be self-assembled in a robust automated manner with high efficiency.

As set forth in further detail herein, lipid-based carriers of biological channels can be assembled at solid-state nanopores having diameters greater than 10 nm. Methods set forth herein can be used for insertion of nanopore proteins in lipid nanodiscs, self-limited assembly of the protein nanopore-nanodiscs with solid-state nanopores, and analytical applications of the hybrid platform, such as nucleic acid detection and sequencing. The resulting platform can be configured to provide the speed and read length characteristics of protein-nanopore-based nucleic acid sequencing systems while providing greater parallelization and system stability available from the use of established semiconductor technologies.

The present disclosure also provides tethered nanopores. In particular, nanopores can be tethered to electrodes or other solid supports in accordance with the present disclosure.

In a particular embodiments, the present disclosure provides a detection apparatus that includes (a) an electrode; (b) a nanopore tethered to the electrode; and (c) a membrane surrounding the nanopore. Multiplex embodiments are also provided. For example a detection apparatus of the present disclosure can include (a) a plurality of electrodes; (b) a plurality of nanopores, each of the nanopores tethered to an electrode in the plurality of electrodes; and (c) a membrane surrounding each of the nanopores.

Also provided is a method of making a detection apparatus. The method can include the steps of: (a) providing a solid support having an array of electrodes; (b) providing a plurality of nanopores; (c) contacting the plurality of nanopores with the array of electrodes to attach individual nanopores to individual electrodes via a first tether, thereby making an array of nanopores that are tethered to electrodes in the plurality of electrodes; and (d) contacting the array of nanopores with membrane material to form a membrane that surrounds each of the nanopores in the array.

Non-limiting advantages of particular embodiments set forth herein for assembly of detection apparatus using tethered nanopores include, for example:

(1) Increased levels of spatial control over nanopore deposition due to the ability to exploit steric exclusion such that one and only one nanopore is accommodated at each electrode.

(2) Highly parallel assembly of multiple nanopores into a detection apparatus.

(3) Ability to achieve nanopore loading efficiencies that beat the limitations of Poisson statistics that hinder standard methods of loading nanopores into multiplex detectors.

BRIEF DESCRIPTION OF THE DRAWINGS

FIG. 1A shows a diagrammatic representation of a protein nanopore that is initially self-assembled within a lipid nanodisc in free solution; FIG. 1B shows the protein nanopore grafted with a nucleic acid; FIG. 1C shows assembly of the protein nanopore-containing nanodisc with the solid-state nanopore due to the nucleic acid chain being driven through the solid-state nanopore until the nanodisc lipids come in contact with the solid state surface.

DETAILED DESCRIPTION

Figure 2A:
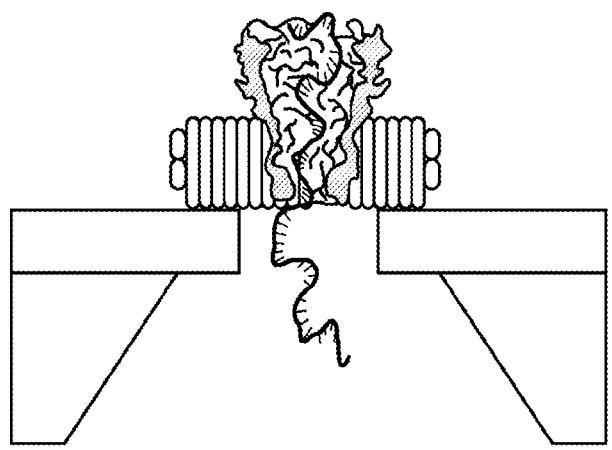
FIG. 2A shows a diagrammatic representation of a 7-10 nm solid-state nanopore assembled with a lipid nanodisc that in turn has a protein nanopore inserted in the lipid membrane, wherein a nucleic acid is grafted to the protein nanopore.

The present disclosure provides a hybrid nanopore system based upon a solid-state nanopore sealed by a protein-pore embedded lipid nanodisc. A conceptual illustration of a particular embodiment is illustrated in FIG. 2.

Current nanopore strand sequencing platforms are based upon free diffusion and insertion of a protein nanopore (also referred to herein as a "biological pore" or "biopore") into a suspended micron sized lipid-bilayer. Various methods have been developed to detect single insertion events, either by monitoring the ionic current or the AC impedance. These approaches rely on additional monitoring circuits/programs which can enlarge the device footprint and increase system complexity. The micron-size lipid bilayer is susceptible to mechanical vibration, adding complexity to device fabrication, shipment, storage and operation. Alternatively, solid-state nanopores with sizes greater than 10 nm are robust and compatible both with high through-put manufacturing and operation, providing a useful platform for nanopore technology. As such, embodiments of the present disclosure utilize solid state nanopores as a platform to assemble single protein nanopores with lipid nanodisc as a rim seal to the solid state nanopore.

Particular embodiments employ insertion of a protein nanopore into a lipid nanodisc carrier and apply electrophoretic force, possibly with a DNA tether, to guide the protein/lipid complex to the solid state nanopore. A lipid nanodisc can be, for example, a 7 to 13 nm-diameter lipid bilayer disc that is optionally stabilized by membrane scaffold protein (MSP), a derivative of apoA-I. It will be understood that a nanodisc can have a diameter that is smaller than 7 nm (e.g. smaller than 6 nm, 5 nm, 4 nm, 2 nm or less in diameter) or larger than 13 nm (e.g. larger than 15 nm, 20 nm, or 25 nm or greater in diameter). Typically, the area of lipid disc used in a method or composition set forth herein is no greater than about 50,000 $nm^2$ or in some cases no greater than about 10,000 $nm^2$ or sometimes no greater than about 1,000 $nm^2$ or even other times no greater than about 500 $nm^2$.

Figure 2B:
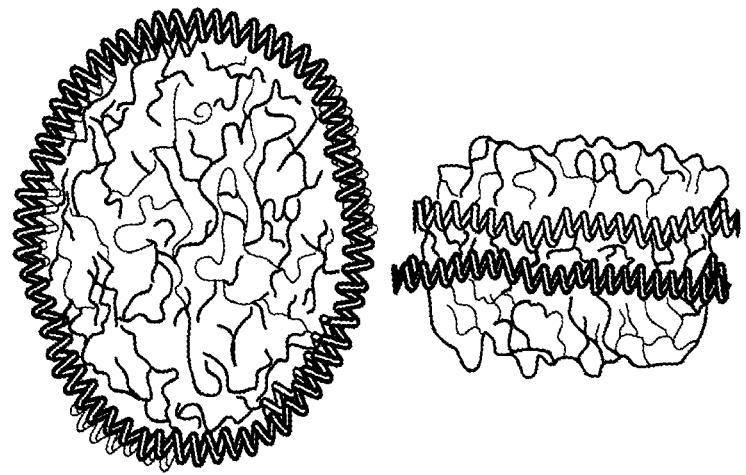
FIG. 2B shows a diagrammatic representation of a 10-13 nm lipid nanodisc (light grey) bounded by a scaffold protein (dark ring).

As exemplified in FIG. 2B, the lipid nanodisc can be composed of a bilayer of lipid molecules surrounded by two parallel belt-like MSPs in which the amphipathic helices of the MSPs stabilize the hydrophobic fatty acid on the edge of the lipid disc. Particularly useful lipid nanodiscs and compositions and methods for their manufacture are set forth, for example, in Nath et al., Biochemistry 46, 2059-2069 (2007), which is incorporated herein by reference.

Lipid nanodiscs can be prepared by mixing MSP with detergent stabilized phospholipid. Self-assembly of nanodiscs occurs during removal of the detergent from the mixture, as set forth below. It has been demonstrated that the presence of MSP confines the shape and size of the lipid nanodisc and provides a narrow size distribution (±3%), excellent reproducibility and exceptional stability in detergent-free aqueous solution. The ratio of MSP to detergent can be selected to achieve desired size and characteristics of the nanodiscs. For example, the number of structural units of the MSP can be varied to allow the nanodisc diameter to be tuned from 9.8 nm to 12.9 nm as set forth in Denisov et al., J. Am. Chem. Soc. 126, 3477-3487 (2004), which is incorporated herein by reference. These diameters are well-matched to solid-state nanopores that can be reliably fabricated with commercially available methods. Nanodiscs can be an effective carrier to incorporate membrane proteins. A number of membrane proteins have been integrated into nanodiscs such as cytochrome, seven-transmembrane segment proteins, bacterial chemoreceptors and human mitochondrial voltage-dependent anion channel protein. Exemplary methods for incorporating membrane proteins into nanodiscs are set forth in Raschle et al., J. Am. Chem. Soc. 131, 17777-17779 (2009). Similar methods can be used to insert protein nanopores, such as α-hemolysin, MspA, Cytolysin and others into lipid nanodiscs. Further examples, of useful protein nanopores are set forth in U.S. Pat. No. 8,673,550, which is incorporated herein by reference.

Coupling between the lipid nanodisc and the solid state nanopore can be facilitated by chemically engineering the lipid/solid interface. For example, the solid surface can be functionalized with cyanopropyl silane, cholesterol, RAFT polymerization, or other materials that bind to or adhere to lipids and/or MSP. Exemplary materials and methods for functionalization of the surfaces are set forth in White et al., J Am Chem Soc 129, 11766-11775 (2007) and Kwok et al., PLOS One DOI: 10.1371/journal.pone.0092880 (2014), each of which is incorporated herein by reference. Similarly, the lipid nanodisc (MSP or lipid) can be engineered to contain coupling or adapter molecules that enable mating with the functionalization on the surface of the solid state nanopore. Such engineering can provide greater than 100 GΩ insulation between the lipid nanodisc and the solid state nanopore. These levels of insulation can facilitate high levels of base discrimination for nucleic acid translocation and sequencing applications. Lipid nanodiscs can also be coupled to a solid state nanopore using reagents and methods set forth herein in the context of tethering lipids to electrodes. Accordingly, tethers that are used to attach lipids to electrodes can be used to couple a nanodisc to a solid state pore.

Figure 3:
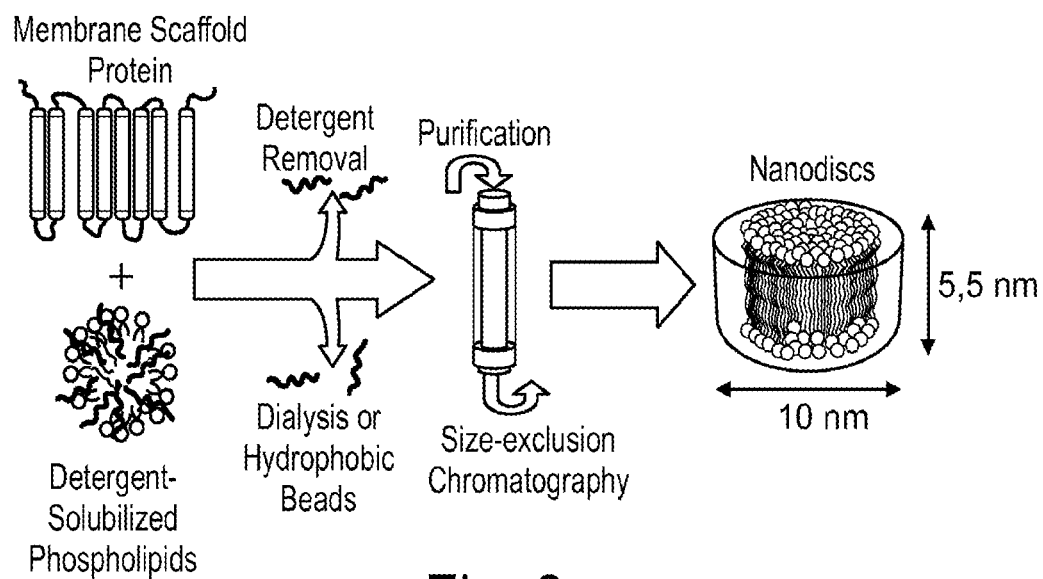
FIG. 3 shows a diagrammatic representation of a process for lipid nanodisc formation.

In particular embodiments, the process for lipid nanodisc formation can be carried out as exemplified in FIG. 3 and further detailed in Baas "Characterization of monomeric human cytochrome P450 3A4 and Cytochrome P450 Reductase in nanoscale phospholipid bilayer discs", University of Illinois at Urbana-Champaign, U.S.A. (2006), ISBN 0542987236, 9780542987236A, which is incorporated herein by reference. As shown in the figure, Membrane Scaffold Protein can be self-assembled with detergent-solubilized phospholipids to form nanodiscs. The self-assembly occurs as the detergent is removed, for example, using Bio-Beads® (Bio-Rad, Hercules Calif.). The product of the assembly reaction can then be purified with size-exclusion chromatography. Optimization of the lipid/protein ratio results in mono-dispersed nanodiscs with size determined by the length of the membrane scaffold protein.

Figure 4:
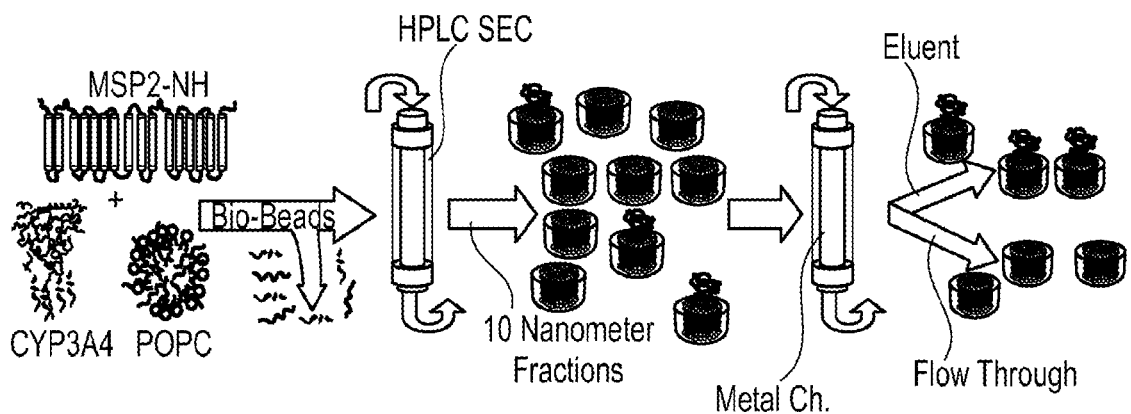
FIG. 4 shows a diagrammatic representation of a lipid nanodisc loading technique in which His-tagged protein (e.g. a porin can be used in place of CYP3A4) is added to the initial mixture, and a metal chelating column is used to separate protein-loaded discs from blank discs.

Insertion of single and even multiple proteins in the nanodiscs can be achieved via an additional purification step that uses a nickel-based affinity matrix to specifically bind a polyhistidine affinity tag on the nanopore protein, for example, using methods similar to those demonstrated in Baas "Characterization of monomeric human cytochrome P450 3A4 and Cytochrome P450 Reductase in nanoscale phospholipid bilayer discs", University of Illinois at Urbana-Champaign, U.S.A. (2006), ISBN 0542987236, 9780542987236A, which is incorporated herein by reference. A diagrammatic representation of a useful method for affinity-based separation of biopore-bearing nanodiscs is shown in FIG. 4.

Figure 5:
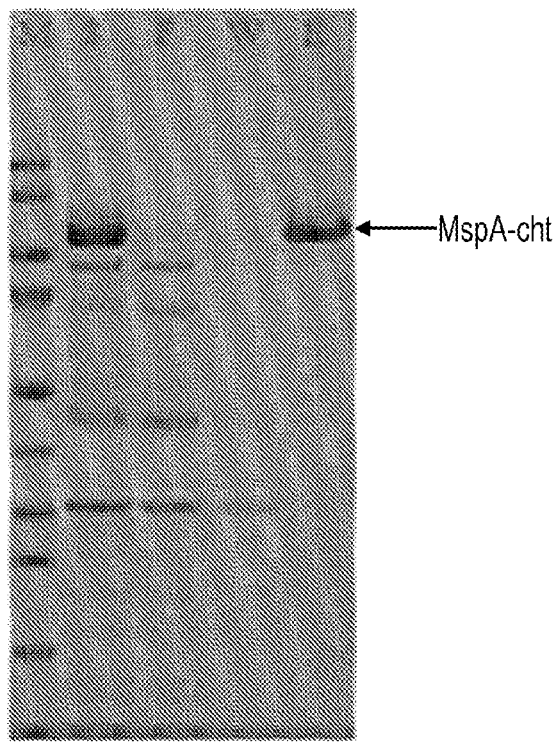
FIG. 5 shows fractions from expression, reconstitution and purification of His-tagged MspA loaded on a polyacrylamide gel. Lane M, protein ladders; Lane S, soluble fraction of cell lysate; Lane F, flow through from Ni-NTA spin column; Lane W, first Wash fraction; Lane E, elution of His-tagged MspA.

Biological pore mutagenesis can be used to optimize protein pores for assembly or use in a composition or method set forth herein. As set forth above, the process of incorporating a protein channel in the nanodisc can benefit from a polyhistidine affinity tag on the protein and from purification of the mixed nanodisc population over a Ni affinity column. Protein engineering and mutagenesis techniques can be used to mutate biological pores and tailor their properties for specific applications. MspA with a C-terminal 6×His tag can be expressed, reconstituted and purified as demonstrated by the SDS-PAGE gel shown in FIG. 5 (Lane M, protein ladders; Lane S, soluble fraction of lysate from cells expressing His-tagged MspA; Lane F, flow through from Ni-NTA spin column; Lane W, 1st Wash fraction from Ni-NTA spin column; Lane E, elution of His-tagged MspA from Ni-NTA spin column). Biological functionality of the purified His-tagged MspA was found to be similar to that of a non-tagged MspA. Other mutations can also be introduced for purification purposes. For example, a cysteine moiety can be introduced into the protein sequence by mutagenesis and used for chemical conjugation to thiol reactive moieties (e.g. maleimides or iodoacetamides) of affinity tags. Exemplary affinity tags include biotin (which can mediate purification via solid-phase streptavidin), DNA and RNA (which can mediate purification via solid-phase nucleic acids having complementary sequences), epitopes (which can mediate purification via solid-phase antibodies or antibody fragments) or other ligands (which can mediate purification via solid-phase receptors for those ligands).

Affinity tags (e.g. His-tags and others set forth herein) and chemical conjugation techniques (e.g. modifications of cysteines set forth above) can be used to attach tethers to nanopores for use in a variety of methods, compositions or apparatus set forth herein. For example, the resulting tethers can be used to attract or attach a nanopore containing nanodisc at or near a solid state nanopore. The tethers can also be used to attach a nanopore to an electrode or other solid-phase support.

Figure 6A:
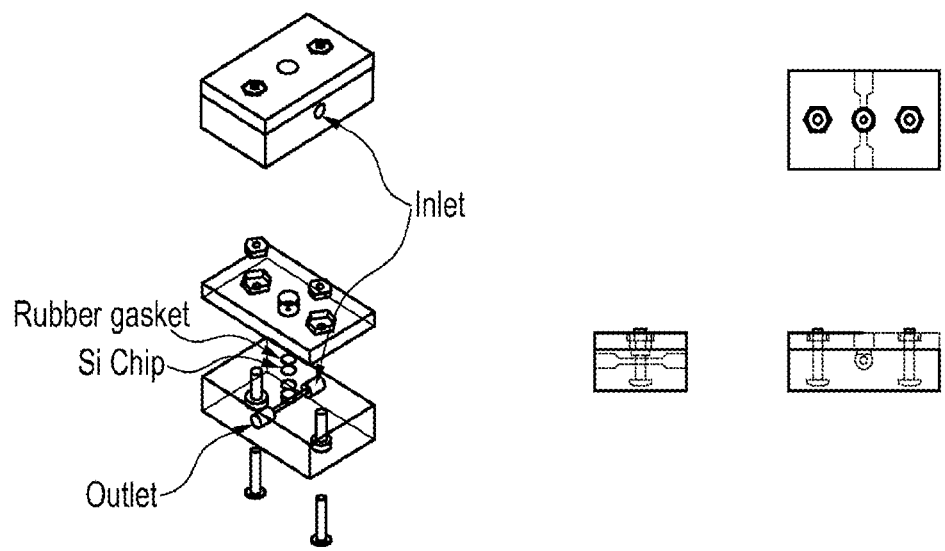
FIG. 6A shows a solid-state nanopore test fixture layout and FIG. 6B shows an implementation of the layout. A nanopore chip ("Si chip") is inserted at the indicated location, and sealed in place by O-ring rubber gasket. Ag/AgCl electrodes on the cis and trans side of the pore provide the current source. The current is measured with an Axopatch 200B amplifier.
Figure 6B:
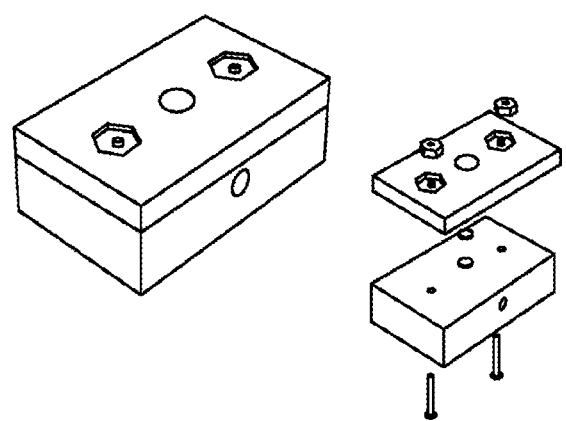
Figure 7:
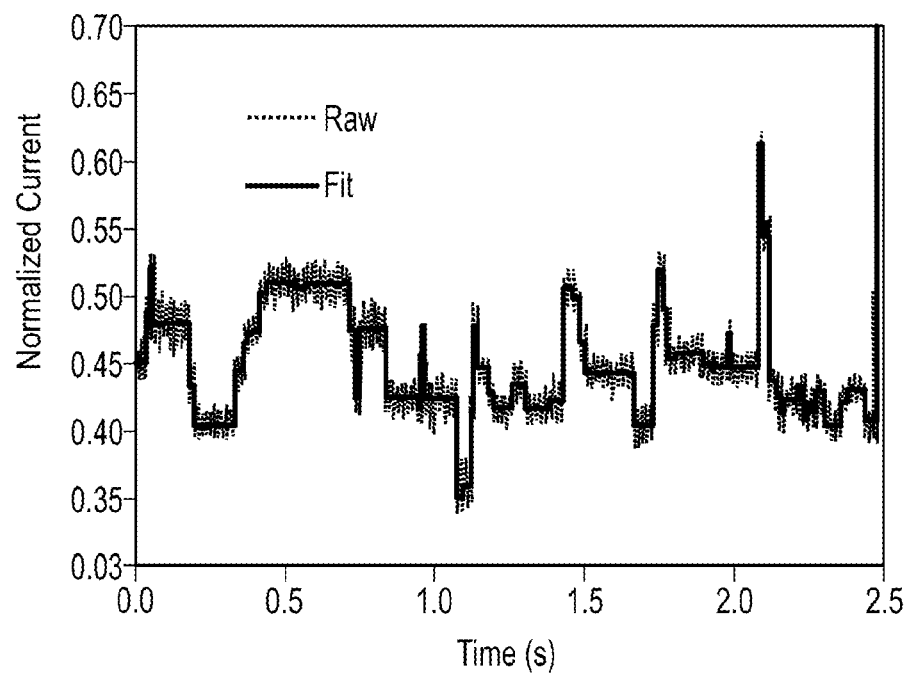
FIG. 7 shows biopore translocation measurement of a 91-mer DNA translocated through MspA biopore inserted into a suspended membrane. The vertical axis is normalized to pore open-state current.

The present disclosure provides a system for data acquisition using one or more hybrid protein-solid state nanopores. An exemplary system is shown in FIG. 6. In this example, the solid-state nanopore is inserted at the indicated location, and sealed in place by an o-ring. Standard Ag/AgCl electrodes on the cis and trans-side of the pore provide the current source. Data from the nanopore can be acquired with an Axopatch 200B amplifier. Preliminary data from a solid self-supporting SiN membrane (no nanopore) has demonstrated greater than 100 GΩ resistance, indicative of a robustly sealed flowcell (less than 0.9 pA leakage current at 200 mV bias). This type of setup is consistent with well-established "standard" setups used to evaluate analytical capabilities in the nanopore art. Representative data from a 91 nucleotide DNA that was translocated through a biological nanopore in strand-displacement mode is shown in FIG. 7.

The disclosure provides a detection apparatus having (a) a solid support including an array of solid state nanopores; (b) a plurality of lipid nanodiscs on the surface of the solid support, wherein each of the lipid nanodiscs forms a seal at each of the solid state nanopores, and wherein the lipid nanodiscs are separated from each other by interstitial regions on the surface of the solid support; and (c) a plurality of protein nanopores inserted in the lipid nanodiscs to create apertures in each of the seals.

The detection apparatus can further include electrodes embedded in the solid support. The electrodes can be used to monitor assembly of nanodiscs and/or protein nanopores into the solid state nanopores. The electrodes can also be used for data collection during analyte detection steps. Electrodes used for monitoring and detection need not be embedded in the solid support and can instead be provided in a separate application-specific integrated circuit (ASIC) chip, for example.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the term "solid support" refers to a rigid substrate that is insoluble in aqueous liquid and incapable of passing a liquid absent an aperture. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers. Particularly useful solid supports comprise modified silicon such as SiN membranes on Si substrate. For some embodiments, solid supports are located within a flow cell apparatus or other vessel.

As used herein, the term "solid state nanopore" refers to a hole that passes through a solid support to allow passage of a liquid or gas. A solid state nanopore will generally have a lumen or aperture that is between about 1 nm and 1 µm in diameter. However, larger or smaller diameters are possible. A solid state nanopore is generally made from materials of non-biological origin. A solid state pore can be of inorganic or organic materials. Solid state pores include, for example, silicon nitride pores, silicon dioxide pores, and graphene pores.

As used herein the term "lipid nanodisc" refers to a lipid bilayer sheet that occupies an area between about 3 $nm^2$ and 3 $\mu m^2$. For example, the area occupied can be at least about 5 $nm^2$, 10 $nm^2$, 50 $nm^2$, 100 $nm^2$, 1,000 $nm^2$, 10,000 $nm^2$, 100,000 $nm^2$, or more. Alternatively or additionally, the area occupied can be at most about 100,000 nm², 10,000 nm², 1,000 nm², 100 nm², 50 nm², 10 nm², 5 nm², or less. A lipid nanodisc can, but need not necessarily, occupy a circular area. The circular area occupied by a nanodisc can have a diameter between about 1 nm and 1 µm. However, larger or smaller areas or diameters are possible. A lipid nanodisc can, but need not necessarily, be flat or planar. In particular conditions a lipid nanodisc can be distinguished from a vesicle or liposome due to the absence of an aqueous lumen for the nanodisc and can be distinguished from a micelle due to the presence of a bilayer in the nanodisc. Several embodiments are exemplified herein using lipid nanodiscs. It will be understood that a nanodisc can be made from other materials as well. For example, a nanodisc can be formed from a non-lipid membrane such as those set forth below.

As used herein the term "membrane" refers to a sheet or other barrier that prevents passage of electrical current or fluids. The membrane is typically flexible or compressible in contrast to solid supports set forth herein. The membrane can be made from lipid material, for example, to form a lipid bilayer, or the membrane can be made from non-lipid material. The membrane can be in the form of a copolymer membrane, for example, formed by diblock polymers or triblock polymers, or in the form of a monolayer, for example, formed by a bolalipid. See for example, Rakhmatullina et al., Langmuir: the ACS Journal of Surfaces and Colloids 24:6254-6261 (2008), which is incorporated herein by reference.

As used herein, the term "interstitial region" refers to an area in a substrate or on a surface that separates other areas of the substrate or surface. For example, an interstitial region can separate one nanopore of an array from another nanopore of the array. The two regions that are separated from each other can be discrete, lacking contact with each other. In many embodiments the interstitial region is continuous whereas the features are discrete, for example, as is the case for an array of pores or apertures in an otherwise continuous surface. The separation provided by an interstitial region can be partial or full separation. Interstitial regions will typically have a surface material that differs from the surface material of the features on the surface. For example, features of an array can have an amount or concentration of lipid material or protein material that exceeds the amount or concentration present at the interstitial regions. In some embodiments the lipid material or protein material may not be present at the interstitial regions.

The interstitial regions can separate lipid nanodiscs by at least 1 nm, 5 nm, 10 nm, 100 nm, 1000 nm or more in an apparatus set forth herein. Alternatively or additionally, the separation may be no more than 1000 nm, 100 nm, 50 nm, 10 nm or 5 nm.

As used herein the term "protein nanopore" refers to a polypeptide, formed as one or more subunits, to create an aperture through a membrane or solid support. Exemplary protein nanopores include α-hemolysin, *Mycobacterium smegmatis* porin A (MspA), gramicidin A, maltoporin, OmpF, OmpC, PhoE, Tsx, F-pilus, SP1 (Wang et al., Chem. Commun., 49:1741-1743, 2013) and mitochondrial porin (VDAC)XX, Tom40, (U.S. Pat. No. 6,015,714 and Derrington et al., Proc. Natl. Acad. Sci. USA, 107:16060 (2010)). "*Mycobacterium smegmatis* porin A (MspA)" is a membrane porin produced by Mycobacteria, allowing hydrophilic molecules to enter the bacterium. MspA forms a tightly interconnected octamer and transmembrane beta-barrel that resembles a goblet and contains a central channel/ pore. Other useful pores are set forth in U.S. Pat. No. 8,673,550. Each of the above nanopore references is incorporated herein by reference.

As used herein, the term "hybrid nanopore" is intended to mean an aperture that is made from materials of both biological and non-biological origins, extending across a barrier such as a membrane for example, that permits hydrated ions and/or water soluble molecules to cross from one side of the barrier to the other side of the barrier. Materials of biological origin are defined above and include, for example, polypeptide and polynucleotide. A biological and solid state hybrid pore includes, for example, a polypeptide-solid state hybrid pore and a polynucleotide-solid state pore.

As used herein the term "tethered" is intended to refer to the state of two items being attached through a linker moiety. The attachment can be covalent, for example, such that an unbroken chain of covalent bonds links the two items. Alternatively, the attachment can be mediated by at least one non-covalent bond, such as a specific binding interaction between a receptor and ligand. Exemplary receptor-ligand pairs include, without limitation, streptavidin (and analogs thereof) and biotin (or analogs thereof); antibody (or functional fragments thereof) and epitopes; lectins and carbohydrates; complementary nucleic acids, nucleic acid binding proteins and their nucleic acid substrates.

A "tether" is a linker moiety that can optionally be used to attach two items. In some configurations a tether is attached to a single item, such as a nanopore, lipid, membrane material or solid support. A tether that is attached to one item can optionally be attached to a second item or used for other purposes. A tether can include nucleotides or nucleic acid material. Alternatively, a tether can be made of a material other than nucleic acid material or can be devoid of nucleotides.

In particular embodiments, a detection apparatus can include solid-state nanopores that form apertures between reservoirs that are separated by the solid support.

In particular embodiments, a seal that is formed over a solid state nanopore prevents flow of fluids and/or flow of electrical current. However, a protein nanopore can form an aperture in the seal.

A protein nanopore can occupy an area on the surface of a lipid nanodisc that is at least about 5 nm, 6 nm, 7 nm, 8 nm, 9 nm, 10 nm or more in diameter. Alternatively or additionally, a protein nanopore can occupy an area on the surface of a lipid nanodisc that is at most about 1 micron, 500 nm, 100 nm, 10 nm, 9 nm, 8 nm, 7 nm, 6 nm, 5, nm or less.

In particular embodiments, a detection apparatus can include at least 10, 100, $1\times10^3$, $1\times10^4$, $1\times10^5$, $1\times10^6$, or more solid state nanopores.

In particular embodiments, a detection apparatus can include lipid nanodiscs covering least 10, 100, $1\times10^3$, $1\times10^4$, $1\times10^5$, $1\times10^6$, or more solid state nanopores. No matter the total number of solid state nanopores, lipid nanodiscs can cover at least 10%, 25%, 50%, 75%, 90%, 95%, 99% or more of the solid state nanopores of a detection apparatus. Accordingly, a detection apparatus can include at least 10, 100, $1\times10^3$, $1\times10^4$, $1\times10^5$, $1\times10^6$, or more nanodiscs.

In particular embodiments, a detection apparatus can include protein nanopores in the lipid nanodiscs covering least 10, 100, $1\times10^3$, $1\times10^4$, $1\times10^5$, $1\times10^6$, or more solid state nanopores. No matter the total number of solid state nanopores, protein nanopores can be inserted into lipid nanodiscs that cover at least 10%, 25%, 50%, 75%, 90%, 95%, 99% or more of the solid state nanopores of a detection apparatus. Accordingly, a detection apparatus can include at least 10, 100, $1\times10^3$, $1\times10^4$, $1\times10^5$, $1\times10^6$, or more nanodiscs having inserted nanopores.

A detection apparatus of the present disclosure can be used to detect any of a variety of analytes including, but not limited to, ions, nucleic acids, nucleotides, polypeptides, biologically active small molecules, lipids, sugars or the like. Accordingly, one or more of these analytes can be present in or passed through the aperture of a protein nanopore in an apparatus set forth herein.

In particular embodiments, a detection apparatus can include a cis reservoir in contact with the array of solid-state nanopores and a trans reservoir in contact with the array of solid state nanopores. The cis and trans reservoirs can contain electrodes located to apply a current through the apertures formed by the protein nanopores. A cis reservoir, trans reservoir or both can be configured to maintain a liquid in bulk fluid communication with a plurality of nanopores in an apparatus set forth herein. Alternatively, one or both of the reservoirs may be in contact with only one or only a subset of the nanopores found in an array or apparatus set forth herein.

In particular embodiments, each of the lipid nanodiscs that covers a solid state nanopore of an array set forth herein will have no more than one protein nanopore inserted therein. However, it is also possible to make and use an apparatus having more than one protein nanopore inserted per solid state nanopore. Similarly, individual nanodiscs, whether covering a solid state nanopore or not, can include no more than one protein nanopore. Alternatively, individual nanodiscs can include more than one protein nanopore.

A lipid nanodisc can be made from any of a variety of membranes or lipids. Suitable lipid bilayers and methods for making or obtaining lipid bilayers are well known in the art and disclosed in, for example, US 2010/0196203 and WO 2006/100484, each of which is incorporated herein by reference. Suitable lipid bilayers include, for example, a membrane of a cell, a membrane of an organelle, a liposome, a planar lipid bilayer, and a supported lipid bilayer. A lipid bilayer can be formed, for example, from two opposing layers of phospholipids, which are arranged such that their hydrophobic tail groups face towards each other to form a hydrophobic interior, whereas the hydrophilic head groups of the lipids face outwards towards the aqueous environment on each side of the bilayer. Lipid bilayers also can be formed, for example, by the method of Montal and Mueller (Proc. Natl. Acad. Sci. USA., 1972; 69: 3561-3566, incorporated herein by reference), in which a lipid monolayer is carried on aqueous solution/air interface past either side of an aperture which is perpendicular to that interface. The lipid is normally added to the surface of an aqueous electrolyte solution by first dissolving it in an organic solvent and then allowing a drop of the solvent to evaporate on the surface of the aqueous solution on either side of the aperture. Once the organic solvent has evaporated, the solution/air interfaces on either side of the aperture are physically moved up and down past the aperture until a bilayer is formed. Other common methods of bilayer formation include tip-dipping, painting bilayers, and patch-clamping of liposome bilayers. A variety of other methods for obtaining or generating membranes are well known in the art and are equally applicable for use in the compositions and methods of the present disclosure (e.g. those pertaining to hybrid nanopores or those pertaining to tethered nanopores). The reagents and methods set forth above can also be used in combination with tethered nanopores or in embodiments where membrane materials are tethered to an electrode or other solid support.

This disclosure further provides a method of making a detection apparatus. The method can include steps of (a) providing a solid support having an array of solid state nanopores; (b) providing a plurality of lipid nanodiscs, wherein the lipid nanodiscs include protein nanopores inserted in the lipid; (c) contacting the plurality of lipid nanodiscs with the array of solid state nanopores to cover individual solid state nanopores of the array with one of the lipid nanodiscs. The method can be used to make a detection apparatus having one or more of the characteristics set forth elsewhere herein.

In particular embodiments step (b) can further include incubating the protein nanopores with lipids under conditions for inserting the protein nanopores in the lipid nanodiscs. For example, the lipids can be detergent solubilized and the conditions can include a technique for removing the detergent from the protein nanopores.

As set forth elsewhere herein, the lipid nanodiscs can be electrically attracted to the solid state nanopores (e.g. via electrophoresis). Optionally, the lipid nanodiscs can include charged tethers to mediate the attraction. As one example, the charged tethers can be nucleic acids, in either naturally occurring form or as a non-naturally occurring analog form. The attachment site of the tether can be used to insert nanodiscs with a particular orientation within the solid state nanopore. This allows the protein nanopore to be oriented in either a forward or reverse direction within the solid state nanopore. Mixes of tether attachment sites can generate any desired ratio of forward to reverse biological pores across an array of solid state nanopores. Similar control of nanopore orientation by placement of tethers can be achieved in embodiments where nanopore tethers are attached to electrodes.

To enhance analyte capture from solution and facilitate two dimensional diffusion of analyte within the plane of the solid state nanopore membrane into the vicinity of the biological nanopore, the solid state nanopore membrane can be derivatized with a compound that reversibly interacts with the analyte. The kinetic on/off rates between the analyte and membrane can be selected to allow a rapid random walk of the analyte across the surface of the solid state nanopore membrane. Examples of such interactions include a cholesterol tag interacting with a lipid monolayer or bilayer, a DNA tag interacting with a DNA surface, and other interactions such as those set forth in Yusko et al., Nat Nanotechnol 6(4): 253-260 (2011). The interaction of the DNA tag with the DNA surface can be facilitated by the use of recombinases that allow walking by strand invasion across the surface of the solid state nanopore membrane.

In some embodiments of the methods, the quantity of the lipid nanodiscs that is contacted with an array of solid state nanopores exceeds the quantity of solid state nanopores in the array. The lipid nanodiscs can include inserted protein nanopores. Thus, Poisson statistics need not be relied upon to obtain solid state nanopores with only one protein nanopore. Instead, saturating amounts of the lipid nanodiscs (with or without inserted protein nanopores) can be contacted with an array of solid state nanopores. For example, the quantity of the lipid nanodiscs (with or without inserted protein nanopores) can exceed the quantity of solid state nanopores by at least 2 fold, 5 fold, 10 fold or more.

The present disclosure provides a detection apparatus that includes (a) an electrode; (b) a nanopore tethered to the electrode; and (c) a membrane surrounding the nanopore.

Multiplex embodiments are also provided. For example a detection apparatus of the present disclosure can include (a) a plurality of electrodes; (b) a plurality of nanopores, each of the nanopores tethered to an electrode in the plurality of electrodes; and (c) a membrane surrounding each of the nanopores.

An electrode used in a method or apparatus of the present disclosure can be made of any of a variety of materials used in nanopore detection devices or other devices for electrochemical processes. In particular embodiments, electrodes are made of a metal. Electrodes can be patterned on a solid support such that the support includes a plurality of electrodes. For example, the solid support can include at least 1, 2, 10, 100, $1\times10^3$, $1\times10^4$, $1\times10^5$, $1\times10^6$, or more electrodes. Alternatively or additionally, a solid support can include no more than $1\times10^6$, $1\times10^5$, $1\times10^4$, $1\times10^3$, 100, 10, 2 or 1 electrodes.

Electrodes that are on a solid support can be separated from each other by interstitial regions that lack the electrode material or are otherwise non-conductive. Accordingly, the electrodes can be spatially and functionally discrete. In some embodiments, each electrode is located within a well or other concave feature on a solid support and the walls of the concave features function as interstitial regions between electrodes. Interstitial regions can separate electrodes on a solid support such that the average pitch (center-to-center) spacing of the electrodes is, for example, at least 5 nm, 10 nm, 25 nm, 50 nm, 100 nm, 1 μm, 10 μm, 100 μm or more. Alternatively or additionally, the pitch can be, for example, no more than 100 μm, 10 μm, 1 μm, 100 nm, 50 nm, 25 nm, 10 nm, 5 nm or less. In some embodiments, the interstitial regions can also lack lipids or nanopores or other materials described herein as being attached to an electrode.

Electrodes used in an apparatus or method set forth herein can have any of a variety of sizes or shapes that achieve a desired use of the detection apparatus. For example, electrodes can have a footprint that is round, rectangular, square, polygonal etc. The area occupied by an electrode can be, for example, at least 25 $nm^2$, 100 $nm^2$, 500 $nm^2$, 1 $\mu m^2$, 50 $\mu m^2$, 100 $\mu m^2$, 1 $mm^2$, or larger. Alternatively or additionally, the area of the electrodes can be, for example, at most 1 $mm^2$, 100 $\mu m^2$, 50 $\mu m^2$, 1 $\mu m^2$, 500 $nm^2$, 100 $nm^2$, 25 $nm^2$, or smaller.

In particular embodiments, an electrode can be covered at least partially by a dielectric pad. Dielectric pads can provide reactive moieties that interact with molecules, such as tether molecules, to achieve attachment of the molecules to the dielectric pad. Silane coupling chemistry is particularly useful for coupling. Exemplary coupling chemistries are set forth in US Pat App. Pub. Nos. 2014/0200158 A1 or 2015/0005447 A1, each of which is incorporated herein by reference. Molecules that are attached to the dielectric pads will be effectively attached to the electrode via the dielectric pad.

A dielectric pad used in a method or apparatus set forth herein can have areas in the range exemplified above for electrodes. In some cases, the dielectric pad will occupy a fraction of the surface of an electrode that is at most, 75%, 50%, 25%, 10%, 5%, 1% or less of the electrode surface. Particularly useful dielectric pads will have an area that is comparable to or smaller than the footprint of a nanopore. As such, the dielectric pad will have a capacity for one and only one nanopore. The resulting steric exclusion allows an array of electrodes having the dielectric pads to be contacted with an excess of nanopores (i.e. a number of nanopores that is larger than the number of electrodes in the array) such that all or most of the electrodes can be attached to nanopores while avoiding the risk of attaching multiple nanopores at individual electrodes that could occur if steric exclusion is not achieved.

Any of a variety of nanopores set forth herein or otherwise known in the art can be used in a tether attachment embodiment set forth herein. Particularly useful nanopores are protein nanopores such as Msp A.

A nanopore can be tethered to an electrode (e.g. via a dielectric pad) using covalent moieties or non-covalent binding moieties. An example of a covalent attachment is when a nucleic acid tether is covalently attached to the nanopore and covalently attached to the dielectric pad. Other tethers can be similarly used for covalent attachment, including for example, non-nucleic acid tethers such as polyethylene glycol or other synthetic polymers. An example, of a non-covalent attachment is when a nanopore has an attached affinity moiety, such as a poly histidine tag, Strep-tag or other amino acid encoded affinity moiety. Affinity moieties can bind non-covalently to ligands on a dielectric pad such as nickel or other divalent cations that bind polyhistidine, or biotin (or analogs thereof) that bind to Strep-tag. In some embodiments, such amino acid affinity moieties need not be used.

An apparatus set forth herein can include any number of tethered nanopores desired. For example, an apparatus can include at least 1, 2, 10, 100, $1\times10^3$, $1\times10^4$, $1\times10^5$, $1\times10^6$, or more tethered nanopores. Alternatively or additionally, an apparatus can include no more than $1\times10^6$, $1\times10^5$, $1\times10^4$, $1\times10^3$, 100, 10, 2 or 1 tethered nanopore.

Any of a variety of membrane materials can be used in a nanopore tethering embodiment set forth herein. Exemplary lipids that can be used include those set forth herein in the context of nanodisc embodiments or in references cited in context of those embodiments. Other useful lipids materials are set forth in U.S. Pat. No. 8,999,716, which is incorporated herein by reference.

In particular embodiments, a membrane can be tethered to an electrode. The membrane can be tethered to an electrode to which a nanopore is also tethered (e.g. via a dielectric pad). The tethers used to attach membrane material to an electrode can be selected from those exemplified herein in regard to nanopore tethers. Tethers with reactive thiols can be particularly useful for attaching to gold containing electrodes. Other tethers are also possible including, for example, tethers with silane or phosphonate reactive groups which can be used to attach to conductive metal oxides (see for example Folkers et al., Langmuir 11:813 (1995), which is incorporated herein by reference). In some embodiments, a different tether material is used for membrane material compared to the tether used for a nanopore. Alternatively, the same tether type can be used for both nanopores and membrane materials. It will be understood that in some embodiments, or in some stages of preparation of a detection apparatus, the membrane material that surround a nanopore need not be tethered to the electrode to which the nanopore is tethered.

In some detection apparatus, particularly those with multiple electrodes, the membrane that surrounds each of the nanopores can form a seal for the electrode to which the nanopore is tethered. The seal can be made to prevent flow of fluids or electrical current from the electrode to which the nanopore is tethered to other electrodes of the detection apparatus. For example, the electrode can occur within a well (or other concave feature) and the membrane can seal the well by forming a continuous sheet that contacts the walls of the well. Thus a chamber is formed within the space defined by the electrode, the walls of the well and the membrane. The chamber can function as a cis or trans chamber depending upon the relative orientation of the electrodes and the orientation of the inserted nanopore.

As set forth in further detail below, a detection apparatus having tethered nanopores can be particularly useful for detection of nucleic acids including detection of nucleic acids in a sequencing method. As such, the detection apparatus can occur in a state where a nucleic acid analyte is located in an aperture formed by the nanopore. The nucleic acid being an analyte that is to be detected is distinct and different from a nucleic acid that may be used as a tether in the apparatus.

The detection apparatus can include other hardware used for detection of nanopores, such as electrodes configured to create a current across a membrane and through a nanopore, an amplifier that is configured to amplify electrical signals generated at the nanopore, a computer coupled to the apparatus to evaluate signals detected from one or more nanopores etc. Hardware useful for detecting signals from nanopores and that can be modified for use in a method set forth herein is described in the art, for example, in U.S. Pat. No. 8,673,550 or 8,999,716; Rosenstein et al., Nano Lett 13, 2682-2686 (2013); or Uddin et al., Nanotechnology 24, 155501 (2013), each of which is incorporated herein by reference.

Also provided is a method of making a detection apparatus. The method can include the steps of: (a) providing a solid support having an array of electrodes; (b) providing a plurality of nanopores; (c) contacting the plurality of nanopores with the array of electrodes to attach individual nanopores to individual electrodes via a first tether, thereby making an array of nanopores that are tethered to electrodes in the plurality of electrodes; and (d) contacting the array of nanopores with membrane material to form a membrane that surrounds each of the nanopores in the array.

Figure 12:
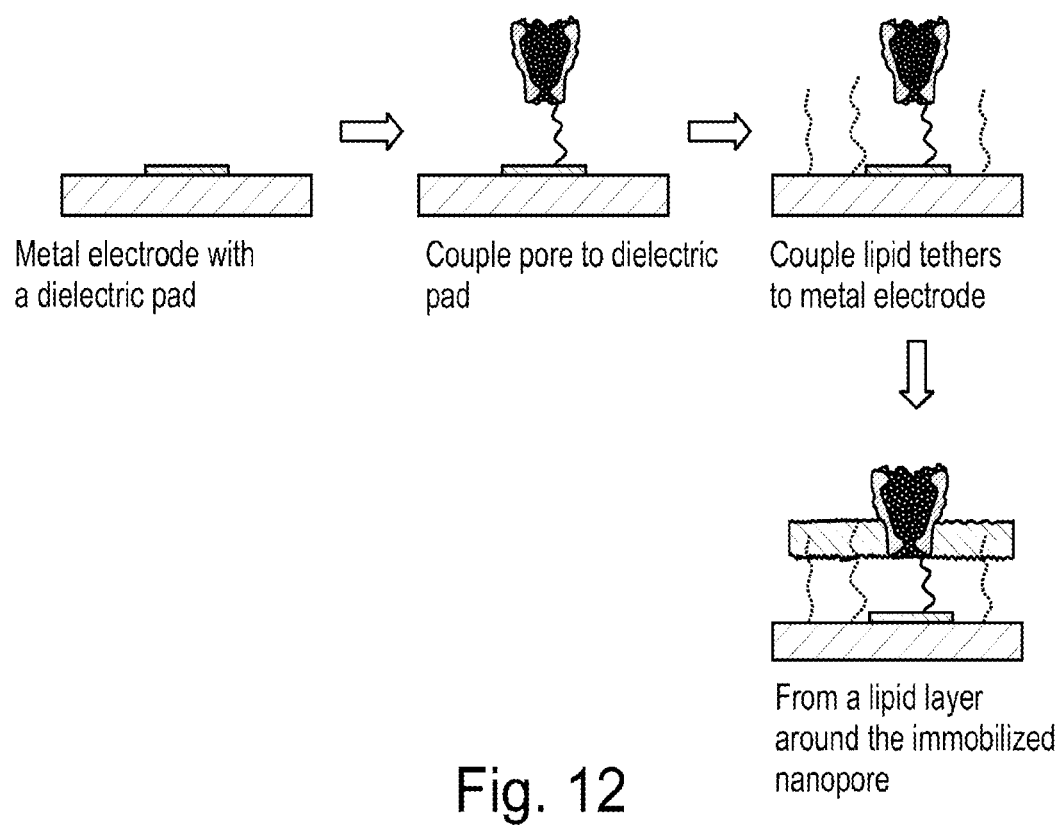
FIG. 12 shows a diagrammatic representation of a method for tethering a nanopore to an electrode, wherein membrane tethers are attached to the electrode after the nanopore is attached to the electrode.

An exemplary embodiment of a method for tethering a nanopore to an electrode is shown in FIG. 12. A metal electrode is provided, the surface of the electrode having a dielectric pad that covers a portion of the surface. For example, the dielectric pad can be an approximately circular pad that is about 10-50 nm in diameter. The dielectric pad can have reactive silanes that are capable of forming a covalent bond with a moiety that is present on a nanopore tether. A nanopore can be chemically modified to include a nucleic acid tether having the moiety. The tether-containing nanopore can then be contacted with the dielectric pad under conditions for the silane to react with the tether to covalently attach the nanopore to the dielectric pad. Once the nanopore has been attached, membrane tethers can be reacted with the metal surface of the electrode. For example, the membrane tethers can include thiols that form covalent bonds with the metal surface. In the last step shown, membrane material (e.g. lipid material) can be contacted with the system under conditions to form a membrane (e.g. lipid bilayer) that surrounds the tethered nanopore and to form covalent bonds between the membrane tethers and lipids in the bilayer. Thus the membrane is also tethered to the electrode.

Figure 13:
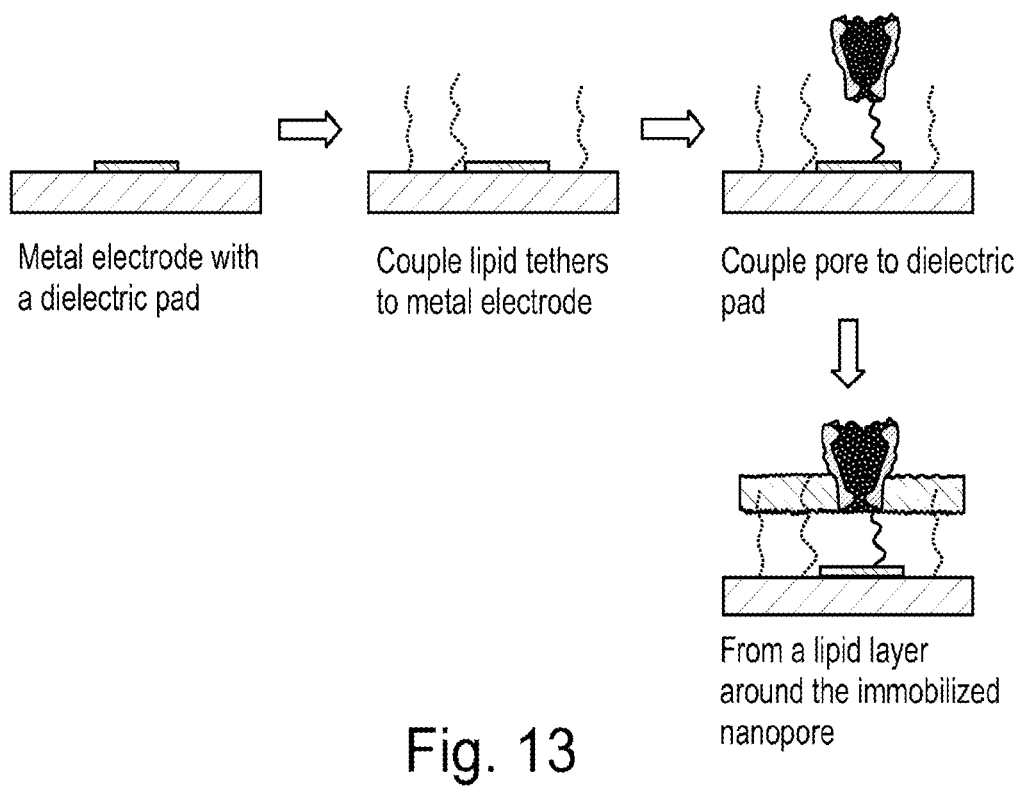
FIG. 13 shows a diagrammatic representation of a method for tethering a nanopore to an electrode, wherein membrane tethers are attached to the electrode before the nanopore is attached to the electrode.

Another embodiment is shown in FIG. 13. The method uses similar components to those used in FIG. 12. However, here the membrane tethers are attached to the metal surface of the electrode prior to attaching the nanopore.

Figure 14:
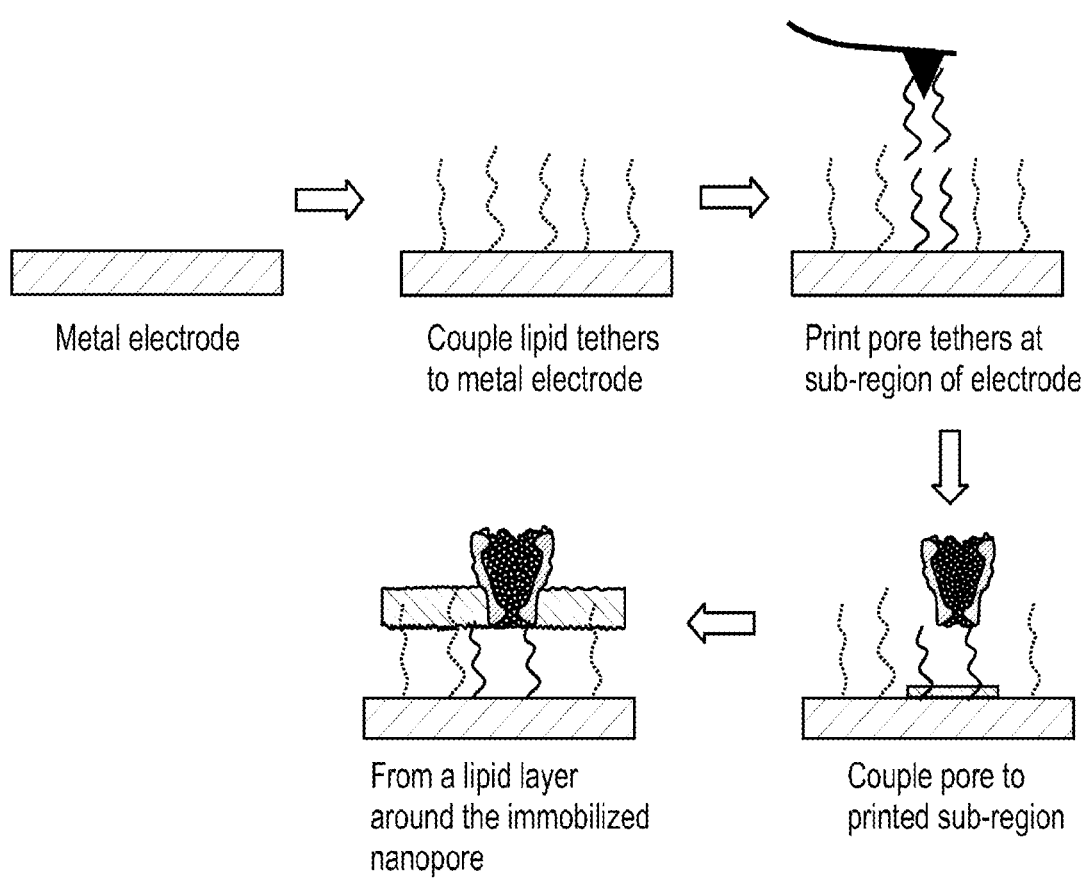
FIG. 14 shows a diagrammatic representation of a method for tethering a nanopore to an electrode, wherein nanopore tethers are attached to the electrode before the electrode is contacted with the nanopore.

A further exemplary embodiment is shown in FIG. 14. In this embodiment, the metal electrode does not include a dielectric pad. The metal electrode is reacted with membrane tethers in a first step. Then a nano-printing technology, such as lithography, is used to attach nanopore tethers to the surface of the metal electrode. The nanopore tethers can be printed in a small area (e.g. approximately circular areas that are about 10-50 nm in diameter). A nanopore can then be contacted with the tether containing electrode under conditions to create a covalent linkage between the nanopore and tether. In the final step, a membrane (e.g. lipid membrane) can be formed around the tethered nanopore and reacted with the membrane tethers to become attached to the electrode.

In particular embodiments, a plurality of nanopores is contacted with a plurality of electrodes in bulk. For example, a solution that includes the nanopores can be contacted with a solid support having multiple electrodes such that the nanopores in the solution are in fluid communication with multiple electrodes. The quantity of nanopores that are contacted with the array of electrodes can exceed the quantity of electrodes in the array. This can be done, for example, to increase the probability that most or all of the electrodes will become tethered to a nanopore. The electrodes can be configured to have a capacity for no more than one nanopore. For example, the electrode can have a surface or surface portion that is relatively small compared to the size of the nanopore. As a result, once a first nanopore has attached to the electrode a subsequent nanopore is sterically excluded from attaching to the same electrode. Thus, an array can include a number of electrodes having a single nanopore that exceeds the number that would be expected from typical Poisson statistics. For example, an array can be loaded with a single nanopore at each of at least 50%, 65%, 75%, 90%, 95%, 99% or more of the electrodes in the array.

Nanopores that are contacted with membrane material can be detergent solubilized. The detergent can then be removed from the protein nanopores to allow a membrane (e.g. lipid bilayer) to surround the nanopores. For example, in situ dialysis can be carried out once the nanopores are attached to the electrode surface. Exemplary in situ dialysis methods and tether compositions are set forth in Giess et al., Biophysical J. 87:3213-3220 (2004), which is incorporate herein by reference.

In some embodiments, nanopores can be electrically attracted to electrodes to facilitate attachment. A nanopore can be attracted based on intrinsic charge. However, it is also possible to use a charged tether, such as nucleic acid, and to attract the tether to the electrode. Exemplary methods for electrically assisted localization of nucleic acids to electrodes are set forth in U.S. Pat. No. 8,277,628, which is incorporated herein by reference.

Any of a variety of tethers described herein or known in the art can be used in a method set forth herein. A particularly useful tether is a nucleic acid tether. In some embodiments, such as those exemplified in FIG. 12 and FIG. 13, a tether can be attached to a nanopore prior to attaching the tether to an electrode. Alternatively, for example as shown in FIG. 14, a nanopore tether can first be attached to an electrode and then the nanopore is reacted with the nanopore tether to create an attachment between nanopore and tether.

A method set forth herein can include a step of attaching membrane material to one or more electrodes via a tether. Particularly useful membrane tethers are bifunctional molecules having a lipophilic domain and a hydrophilic spacer. The lipophilic domain (e.g. phospholipid, cholesterol, or phytanyl) inserts into a membrane and the hydrophilic spacer can attach to a solid support, such as an electrode. Exemplary membrane tethers are set forth, for example, in Giess et al., Biophysical J. 87:3213-3220 (2004), which is incorporate herein by reference.

The present disclosure further provides a method of sequencing nucleic acids. The method can include steps of (a) providing a detection apparatus having: (i) a solid support including an array of solid state nanopores; (ii) a plurality of lipid nanodiscs on the surface of the solid support, wherein each of the lipid nanodiscs forms a seal at each of the solid state nanopores, and wherein the lipid nanodiscs are separated from each other by interstitial regions on the surface of the solid support; and (iii) a plurality of protein nanopores inserted in the lipid nanodiscs to create apertures in each of the seals; and (b) detecting passage, through the apertures in each of the seals, of (i) a nucleic acid, (ii) a series of nucleotides removed from the nucleic acid, or (iii) a series of probes derived from nucleotides incorporated into the nucleic acid, thereby determining the sequence of the nucleic acid.

Also provided is a method of sequencing nucleic acids that includes steps of: (a) providing a detection apparatus that includes (i) a plurality of electrodes, (ii) a plurality of nanopores, each of the nanopores tethered to an electrode in the plurality of electrodes, and (iii) a membrane surrounding each of the nanopores; and (b) detecting passage, through each of the nanopores, of (i) a nucleic acid, (ii) a series of nucleotides removed from the nucleic acid, or (iii) a series of probes derived from nucleotides incorporated into the nucleic acid, thereby determining the sequence of the nucleic acid.

A nucleic acid detected in the methods of the present disclosure can be single stranded, double stranded, or contain both single stranded and double stranded sequence. The nucleic acid molecules can originate in a double stranded form (e.g., dsDNA) and can optionally be converted to a single stranded form. The nucleic acid molecules can also originate in a single stranded form (e.g., ssDNA, ssRNA), and the ssDNA can optionally be converted into a double stranded form. Exemplary modes of translocating polynucleotides through a pore are set forth in WO 2013 057495, which is incorporated herein by reference.

In some embodiments, sequencing can be carried out by passing a nucleic acid through a protein nanopore and detecting electrical signals indicative of the passage of a particular nucleotide or series of nucleotides (e.g. a "word" consisting of 2, 3 4, 5 or more nucleotides). In some embodiments, a certain level of controlled translocation of a polynucleotide through a nanopore can be achieved under the guidance of a molecular motor, such as a helicase, translocase, or polymerase against an electric potential difference. Molecular motors can move the polynucleotide in a step-wise manner, normally with one or more nucleotides per step. This controlled ratcheting slows the polynucleotide translocation through the nanopore from a native rate of μsec/nucleotide to msec/nucleotide.

A method of detection can utilize a potential difference across a barrier (e.g., a membrane). The potential difference can be an electric potential difference, chemical potential difference, or an electrochemical potential difference. An electric potential difference can be imposed across the barrier (e.g., membrane) via a voltage source that injects or administers current to at last one of the liquid pools. A chemical potential can be imposed across the barrier via a difference in ionic composition of the two pools. An electrochemical potential difference can be established by a difference in ionic composition of the two pools in combination with an electrical potential. The different ionic composition can be, for example, different ions in each pool or different concentrations of the same ions in each pool.

The application of an electrical potential across a pore to force the translocation of a nucleic acid through the pore is well known in the art and can be used in accordance with the present apparatus and methods (Deamer et al., Trends Biotechnol., 18:147-151 (2000); Deamer et al., Acc Chem Res., 35:817-825 (2002); and Li et al., Nat Mater., 2(9):611-615 (2003), each of which s incorporated herein by reference). A method set forth herein can be carried out with a voltage applied across a pore. The range for the voltage can be selected from 40 mV to upwards of 1 V. Typically a method set forth herein will run in the range of 100 to 200 mV. In specific instances, the method is run at 140 mV or 180 mV. The voltages are not required to be static during the motion of the motor. The voltage polarity is typically applied such that the negatively charged nucleic acid is electrophoretically driven into the pore. In some instances, the voltage can be reduced, or the polarity reversed, to facilitate appropriate function.

In some instances, the application of pressure differentials can be utilized to force translocation of a nucleic acid through a pore. Pressure differentials can be used in place of electrical potentials or other potential differences in methods exemplified herein. Alternatively, a pressure differential can be used in combination with electrical potentials or other potential differences in methods exemplified herein.

The methods of the present disclosure can produce one or more signals that correspond to the translocation of one or more nucleotides through a pore. Accordingly, as a target polynucleotide, or as a mononucleotide or probe derived from the target polynucleotide or mononucleotide, transits through a pore the current across the barrier changes due to base-dependent (or probe dependent) blockage of the constriction, for example. The signal from that change in current can be measured using any of a variety of methods as described herein or as otherwise known in the art. Each signal is unique to the species of nucleotide(s) (or probe) in the pore such that the resultant signal can be used to determine a characteristic of the polynucleotide. For example, the identity of one or more species of nucleotide(s) (or probe) that produces a characteristic signal can be determined. Signals useful in the methods of the present invention include, for example, electrical signals and optical signals. In some aspects, the electrical signal can be a measurement of current, voltage, tunneling, resistance, voltage, conductance; or transverse electrical measurement (see WO 2013/016486, which is incorporated herein by reference). In some aspects, the electrical signal is an electrical current passing through a pore.

Optical signals useful in the methods of the present disclosure include, for example, fluorescence and Raman signal. The optical signals can be generated by coupling the target nucleotide with an optical signal generating label, for example, a fluorescent moiety or a Raman signal generating moiety. For example, in dela Torre et al., Nanotechnology, 23(38):385308 (2012), the optical scheme of Total Internal Reflection Fluorescence (TIRF) microscopy was employed to illuminate a wide area of the TiO2-coated membrane. In Soni et al., Rev Sci Instrum., 81(1):014301 (2010), a method was used for integrating two single-molecule measurement modalities, namely, total internal reflection microscopy and electrical detection of biomolecules using nanopores. The above two references are incorporated herein.

As described herein, the nanopores (whether hybrid nanopores or tethered nanopores) can be coupled with a detection circuit, including, for example, a patch clamp circuit, a tunneling electrode circuit, or a transverse conductance measurement circuit (such as a graphene nanoribbon, or a graphene nanogap), to record the electrical signals in methods of the present disclosure. In addition, the pore can also be coupled with an optical sensor that detects labels, for example, a fluorescent moiety or a Raman signal generating moiety, on the polynucleotides.

Molecular motors can use the energy of nucleotide hydrolysis to drive the translocation of a target polynucleotide through a nanopore. A helicase is an example in which ATP hydrolysis is the energy source for polynucleotide translocation. For example, in one model a single stranded polynucleotide is held in a negatively charged cleft that separates the two RecA domains of a helicase from a third domain. In the absence of ATP, a bookend residue (e.g., Trp501 in HCV helicase) and a clamp residue (e.g., Arg393 in HCV helicase) prevent the single stranded polynucleotide from sliding through a cleft. Upon ATP binding, the RecA domains rotate, moving the positively charged Arg-clamp. The Arg-clamp attracts the negatively charged single stranded polynucleotide, which in turn clears the bookend. The single stranded polynucleotide is then repelled by the negatively charged cleft, and the single stranded polynucleotide translocates through the helicase until ATP is hydrolyzed. Therefore, in this exemplary model, the polynucleotide translocation through a helicase involves at least two steps: a first step where the helicase binds to ATP and undergoes a conformational change, and a second step where ATP is hydrolyzed and the polynucleotide translocates through the helicase.

Other detection techniques that can be applied to an apparatus set forth herein include, but are not limited to, detecting events, such as the motion of a molecule or a portion of that molecule, particularly where the molecule is DNA or an enzyme that binds DNA, such as a polymerase. For example, Olsen et al, JACS 135: 7855-7860 (2013), which is incorporated herein by reference, discloses bioconjugating single molecules of the Klenow fragment (KF) of DNA polymerase I into electronic nanocircuits so as to allow electrical recordings of enzymatic function and dynamic variability with the resolution of individual nucleotide incorporation events. Or, for example, Hurt et al., JACS 131: 3772-3778 (2009), which is incorporated herein by reference, discloses measuring the dwell time for complexes of DNA with the KF atop a nanopore in an applied electric field. Or, for example, Kim et al., Sens. Actuators B Chem. 177: 1075-1082 (2012), which is incorporated herein by reference, discloses using a current-measuring sensor in experiments involving DNA captured in a α-hemolysin nanopore. Or, for example, Garalde et al., J. Biol. Chem. 286: 14480-14492 (2011), which is incorporated herein by reference, discloses distinguishing KF-DNA complexes based on the basis of their properties when captured in an electric field atop an α-hemolysin pore. Other references that disclose measurements involving α-hemolysin include the following, all to Howorka et al., which are incorporated herein by reference: PNAS 98: 12996-13301 (2001); Biophysical Journal 83: 3202-3210 (2002); and Nature Biotechnology 19: 636-639 (2001).

U.S. Pat. No. 8,652,779 to Turner et al., which is incorporated herein by reference, discloses compositions and methods of nucleic acid sequencing using a single polymerase enzyme complex including a polymerase enzyme and a template nucleic acid attached proximal to a nanopore, and nucleotide analogs in solution. The nucleotide analogs include charge blockade labels that are attached to the polyphosphate portion of the nucleotide analog such that the charge blockade labels are cleaved when the nucleotide analog is incorporated into a growing nucleic acid. According to Turner, the charge blockade label is detected by the nanopore to determine the presence and identity of the incorporated nucleotide and thereby determine the sequence of a template nucleic acid. U.S. Patent Publication No. 2014/0051069 which is incorporated herein by reference, is directed to constructs that include a transmembrane protein pore subunit and a nucleic acid handling enzyme.

Example I

The two major thrusts of the experimental design are to: (a) engineer, synthesize and purify the protein-nanodisc complex; and (b) assemble the complex on the solid state nanopore platform by electrophoretic forces. The electrophoretic driving force can be enhanced by attaching polyelectrolyte or DNA molecule on the disc or pore-forming protein. Additional surface treatment may be required to improve the insulation on the lipid disc-solid nanopore interface.

Specific Aim #1: Demonstrate Incorporation of MspA Nanopore into Lipid Nanodisc

Milestones: (a) Assemble and characterize blank lipid nanodisc; (b) Engineer MspA protein with His-tag for the purpose of separation and purification; (c) Incorporate MspA protein into lipid nanodisc, purify the product and characterize the morphology.

Synthesize Bio-Pore Incorporated Lipid Nanodisc

Blank lipid nanodiscs are synthesized by titration of lipid and MSP ratio. The experimental approach was reviewed above in connection with FIG. 3. Biopore mutants with C-terminal His-tags are prepared. The His-tagged biopore mutants are added into the nanodisc precursor mixture before the detergent is removed so that the biopore incorporation will take place during the lipid nanodisc self-assembly process. Excess amount of nanodisc component are used to ensure high yield of incorporation. The nanopore-nanodisc complex is separated from empty nanodiscs by a His-tag affinity column. The whole process is monitored and analyzed by size exclusion chromatography (SEC) and sodium dodecylsulfate polyacrylamide gel electrophoresis (SDS-PAGE), and further characterized by liquid-phase atomic force microscopy and transmission electron microscopy.

Specific Aim #2: Achieve >100 GΩ Seal of Lipid Nanodisc Inserted in Solid State Nanopore Milestones: (a) Establish nanopore and electrophoresis infrastructure; (b) Electrophoretically assemble blank lipid-nanodisc onto solid state nanopore; (c) If necessary, chemically functionalize solid state nanopore to ensure >100 GΩ seal; (d) Demonstrate MspA biological pore activity in the hybrid system.

Build Solid State Nanopore System

The fabrication methods for solid state nanopore have historically utilized energized beam drilling, for example, with an electron beam in a Transmission Electron Microscope (TEM)(see, for example, Storm et al., Nature Materials 2, 537-540 (2003), incorporated herein by reference), a Ga ion beam in a Focused Ion Beam (FIB))(see, for example, Patterson et al., Nanotechnology 19, 235304 (2008), incorporated herein by reference) or a Helium Ion Beam (HIB) (see, for example, Yang et al., Nanotechnology 22, 285310 (2011), incorporated herein by reference). A commercial supply of 7-10 nm nanopores will be used for initial demonstration and system development. Initial prototyping of the required equipment is carried out as set forth above in relation to FIG. 6A and FIG. 6B. Electrophysiology tools such as patch-clamp amplifier and electrochemistry workstations, and a cleanroom facility are used for additional nanofabrication work.

Achieve Lipid Nanodisc Sealed Nanopore with >100 GΩ Resistance

Figure 8:
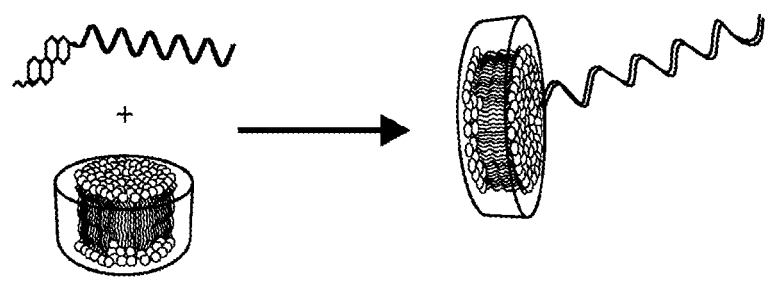
FIG. 8 shows a reaction in which a lipid nanodisc is incubated with cholesterol-TEG DNA to produce a DNA tether on the nanodisc. The DNA tether can be used to electrophoretically pull the lipid nanodisc over a solid state nanopore.

Electrophoretically driven translocation of biomolecules through solid state nanopore has been extensively studied in the past decade. The same strategy can be applied to seal the solid state nanopore with a relatively large sized lipid nanodisc, leaving the incorporated protein nanopore as the only pathway for ionic current and the only pathway for analytes that are to be detected by passage through the pore. The efficiency of sealing is tested with blank lipid nanodiscs (without biopores). Since the lipid nanodisc is lightly charged, a DNA molecule derivatized with cholesterol-TEG can be utilized to improve the electrophoresis effect of capturing lipid nanodisc. Cholesterol tagged DNA tends to bind to the lipid membrane by inserting the hydrophobic cholesterol unit into the membrane. A diagrammatic representation of a blank nanodisc having a nucleic acid tether is shown in FIG. 8.

The electrical field guides the tether-containing nanodisc by capturing the highly charged DNA chain. The capture probability is also affected by nanopore size, ionic strength, voltage and viscosity, which can be adjusted to achieve desired loading. Multiple insertions of DNA tethers into a single nanodisc are possible at this intermediate step, but should not affect the ability to assess the sealing efficiency between the nanodisc and the solid state nanopore surface.

Figure 9:
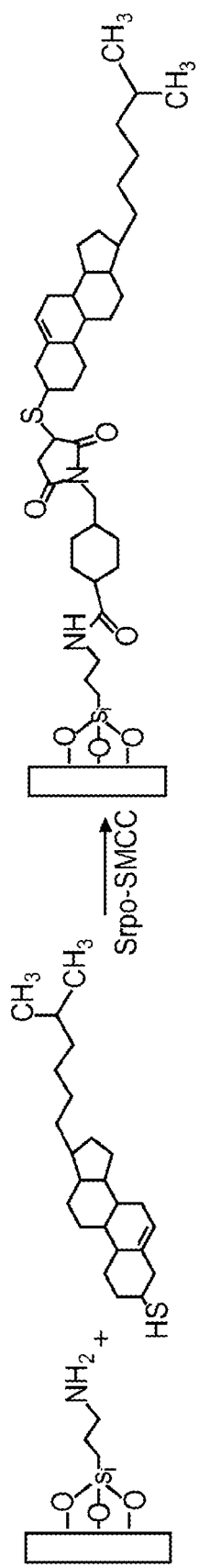
FIG. 9 shows a method for enhanced coupling between a lipid nanodisc and a solid state nanopore. The $Si_3N_4$ surface of the solid support is first treated with an organosilane, followed by a cholesterol derivative.

Additional modifications may be used to achieve a >100 GΩ seal, for example, in embodiments where a seal is not created entirely via electrophoretic action. If necessary, the solid-state nanopore can be functionalized to seal interface leakage pathways. Ensuring hydrophobicity of the interface can prevent the transport of solvated ions. One technique is to coat the top surface of the solid state nanopore with cholesterol derivatives which ensure that the surface is hydrophobic, while also inserting their hydrophobic terminal groups into the membrane. Specific surface chemistry that can be used is shown in FIG. 9.

Another approach is local tethering of the lipid nanodisc, for example, as described in Stackmann Science 271, 43-48 (1996); Steinem et al. Biochim. Biophys. Acta, 1279, 169-180 (1996); Vallejo, Bioelectrochemistry 57, 1-7 (2002); and Avanti Polar Lipids, Inc. (October 2013), "Preparation of Liposomes", each of which is incorporated herein by reference. Alternatively or additionally, the entire surface of the $Si_3N_4$ chip can be coated with a membrane, for example, as described in Yusko et al., Nature Nanotech. 6, 253 (2011), which is incorporated herein by reference. The MspA biopore can then be inserted directly after formation of this membrane coating. Steric hindrance can be exploited to ensure that only a single porin can be inserted into each aperture, and the effective conversion of diffusion from 3 dimensional (i.e. in solution) to 2 dimensional (i.e. in the membrane) can provide adequate insertion efficiency. Large unilamellar vesicles with diameter of ~100 nm can be obtained (see, for example, Avanti Polar Lipids, Inc. (October 2013), "Preparation of Liposomes", which is incorporated herein by reference) and can bridge smaller solid state nanopores (e.g. the ~10 nm nanopores described in this Example).

Additionally, chemical functionalization of the solid-state nanopore may be done to prevent any residual leakage pathway along the interface between the lipid nanodisc and solid state nanopore. Thus, the top surface of the solid state nanopore, which the lipid disc will be in contact with, can be chemically functionalized with hydrophobic self-assembled molecules. Exemplary moieties that can be used for functionalization are cholesterol derivatives which can insert their hydrophobic portion into the membrane, as a result, preventing hydrated ion transport along the interface. Useful surface chemistry to conjugate cholesterol derivative onto solid substrate, is exemplified in FIG. 9.

Surface functionalization may alter the electrical characteristic of the solid state nanopore. The effect can be beneficial by reducing the sticking events by DNA interaction with the solid surface. However, the increase in solid state nanopore hydrophobicity may impact its transport properties (see, for example, Powell et al., Nature Nanotechnology 6, 798-802 (2011), which is incorporated herein by reference. The two effects can be balanced to achieve optimal system performance).

Test Biopore Activity as a Part of the Hybrid Nanopore Device

Specific Aim #2b will demonstrate the assembly of a lipid nanodisc/biopore complex onto a solid state nanopore. The electrical characterization of the hybrid nanopore, noise level and the stability can be characterized under nucleic acid sequencing conditions. The hybrid nanopore may possess higher noise than a conventional protein nanopore device, mainly contributed by the capacitive coupling through the silicon supporting substrate. See, for example, Waggoner et al., Journal of Vacuum Science & Technology B 29, 032206 (2011), which is incorporated herein by reference. The noise level can be optimized by resin passivation of the fluidic contact area, or adding micron thick SiO2 between the $Si_3N_4$ film and the Si substrate, for example, using techniques and materials set forth in Rosenstein et al., Nature Methods 9, 487-492 (2012), which is incorporated herein by reference. Current nanopore sequencing chemistry contains polymerase, ATP, and salt in close to neutral pH buffer, which is not expected to affect the stability of s lipid disc/biopore complex. The performance of the hybrid nanopore can be benchmarked against a conventional lipid-supported biopore in order to characterize its performance.

Example II

This Example describes progress on specific aim #1 of Example I. More specifically, protocols were established to (a) assemble and characterize blank lipid nanodiscs with 10-13 nm diameter, and (b) incorporate MspA nanopore proteins into lipid nanodiscs and characterize the morphology of the complex.

Figure 10:
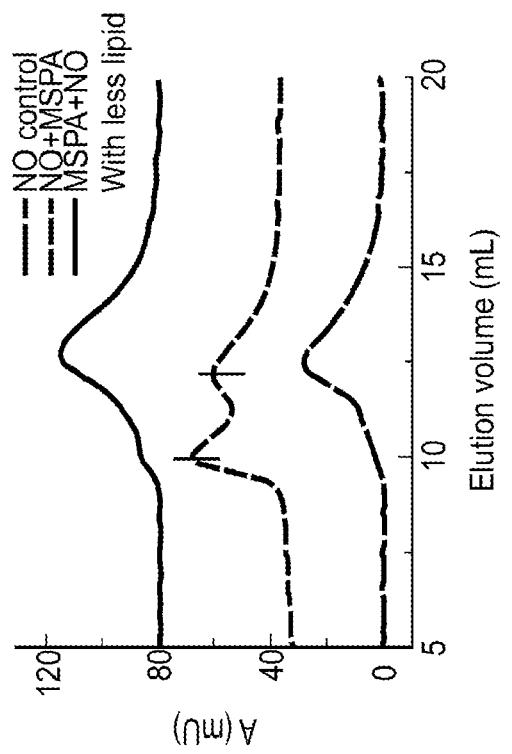
FIG. 10 shows results of optimization of a protocol for inserting of MspA into a lipid nanodisc.

Fast protein liquid chromatography (FPLC) was used to optimize nanodisc formation and MspA insertion as shown in FIG. 10. The bottom trace (black) is for nanodiscs only, showing a well-defined elution peak from an FPLC instrument. Adding MspA to the precursor mix destabilized the reaction and resulted in a second elution peak at higher molecular weight as shown by the middle trace (red). Behavior was similar to that of pure nanodisc synthesis in the presence of excess lipid. Although not necessarily intending to be limited by hypothesis, the surfactant required to stabilize the MspA protein in solution appears to be interacting with the nanodisc self-assembly process. By reducing the amount of lipid used during synthesis by ⅓ normal behavior was recovered as shown by the top trace (blue).

Figure 11A:
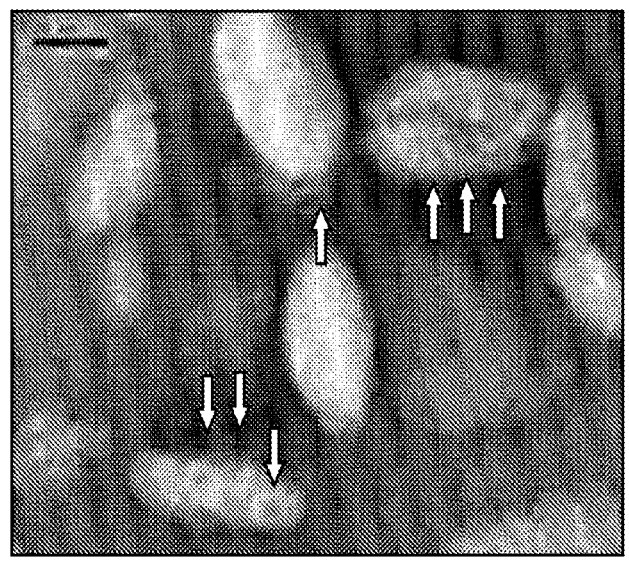
FIG. 11A shows a TEM image of the high molecular weight elution fraction from the middle trace of FIG. 10.
Figure 11B:
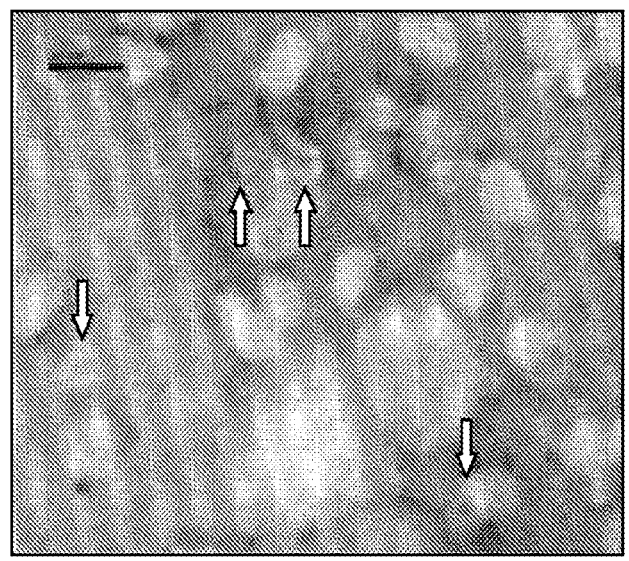
FIG. 11B shows a TEM image of the low molecular weight elution fraction from the middle trace of FIG. 10. Sites of MspA insertion are indicated with arrows.

In addition, Transmission electron microscopy (TEM) characterization was performed on the two elution fractions (A and B) from FIG. 10. The samples were stained with uranyl acetate prior to TEM imaging to enhance contrast. The resulting TEM images are shown in FIG. 11. Apparent insertion of MspA (discs with dark dots) was observed in both samples, with heavy agglomeration in the high MW fraction as expected. TEM images of blank nanodiscs (not shown) did not exhibit such features. Further confirmation of MspA insertion can be obtained through protein electrophoresis, and via metal column purification of the product, as documented in Specific Aim #1 of Example I.

The above results confirm establishment of a protocol for synthesis of bare nanodiscs. Furthermore, the results provide proof-of-principle confirmation of MspA insertion in self-assembled nanodiscs.

Throughout this application various publications, patents or patent applications have been referenced. The disclosure of these publications in their entireties are hereby incorporated by reference in this application.

The term comprising is intended herein to be open-ended, including not only the recited elements, but further encompassing any additional elements.

A number of embodiments have been described. Nevertheless, it will be understood that various modifications may be made. Accordingly, other embodiments are within the scope of the following claims.

What is claimed is:

1. A method of sequencing a target nucleic acid, comprising:
   (a) providing an apparatus comprising:
      (i) a solid support comprising an array of solid state nanopores,
      (ii) a plurality of lipid nanodiscs on a surface of the solid support, wherein each of the lipid nanodiscs comprises a lipid bilayer and forms a seal at each of the solid state nanopores, and wherein the lipid nanodiscs are non-contiguous from each other on the surface of the solid support, and
      (iii) a plurality of protein nanopores inserted in the lipid nanodiscs to create apertures in each of the seals; and
   (b) detecting passage of a nucleic acid species through the apertures, wherein the nucleic acid species is selected from the group consisting of:
      (i) the target nucleic acid,
      (ii) a series of nucleotides removed from the target nucleic acid, and
      (iii) a series of probes derived from nucleotides incorporated into the target nucleic acid;
   thereby determining the sequence of the target nucleic acid.

2. The method of claim 1, wherein (b) comprises detecting an electrical signal.

3. The method of claim 1, wherein the passage of a nucleic acid species is achieved under the guidance of a molecular motor against an electric potential difference, wherein the molecular motor is selected from the group consisting a helicase, a translocase, and a polymerase.

4. The method of claim 1, wherein the target nucleic acid comprises a single-stranded polynucleotide.

5. The method of claim 1, wherein the lipid bilayer disc is stabilized with a membrane scaffold protein (MSP).

6. The method of claim 1, wherein each of the lipid nanodiscs comprises no more than one protein nanopore.

7. The method of claim 1, wherein the lipid nanodiscs form seals for at least 50% of the solid state nanopores, and wherein the protein nanopores are inserted in at least 50% of the lipid nanodiscs.

8. The method of claim 1, wherein the apparatus comprises a cis reservoir in contact with the array of solid state nanopores and a trans reservoir in contact with the array of solid state nanopores, and wherein the cis reservoir and the trans reservoir comprise electrodes to apply a current through the apertures formed by the protein nanopores.

9. The method of claim 1, wherein the apparatus comprises an amplifier configured to amplify electrical signals generated at the protein nanopores.

10. The method of claim 1, wherein the solid state nanopores each have an aperture diameter from 7 nm to 5 microns.

11. The method of claim 1, wherein each of the protein nanopores occupy an area in the nanodisc having a diameter from 5 nm to 1 micron.

12. The method of claim 1, wherein the lipid nanodiscs each have a diameter from 7 nm to 1 micron.

13. The method of claim 1, wherein the lipid nanodiscs each occupy an area of no more than 50,000 $nm^2$ on the surface of the solid support.

14. The method of claim 1, wherein the array comprises at least 1000 solid state nanopores, at least 1000 lipid nanodiscs, and at least 1000 protein nanopores.

15. The method of claim 1, wherein the lipid nanodiscs are separated from each other by at least 5 nm.

16. The method of claim 1, wherein the surface of the solid support separating the lipid nanodiscs is devoid of any lipid material.

17. The method of claim 1, wherein the target nucleic acid is a double-stranded polynucleotide.

18. The method of claim 1, wherein the target nucleic acid is DNA.

19. The method of claim 1, wherein the target nucleic acid is RNA.

20. A method of sequencing a target nucleic acid comprising a single-stranded polynucleotide, comprising:
   (a) providing an apparatus comprising:
      (i) a solid support comprising an array of solid state nanopores,
      (ii) a plurality of lipid nanodiscs on a surface of the solid support, wherein each of the lipid nanodiscs comprises a lipid bilayer and forms a seal at each of the solid state nanopores, and wherein the lipid nanodiscs are non-contiguous from each other on the surface of the solid support, and
      (iii) a plurality of protein nanopores inserted in the lipid nanodiscs to create apertures in each of the seals; and
   (b) detecting passage of a nucleic acid species through the apertures by detecting an electrical signal, wherein the nucleic acid species is selected from the group consisting of:
      (i) the target nucleic acid,
      (ii) a series of nucleotides removed from the target nucleic acid, and
      (iii) a series of probes derived from nucleotides incorporated into the target nucleic acid;
   thereby determining the sequence of the target nucleic acid.

* * * * *